United States Patent
Lai et al.

(10) Patent No.: US 8,882,993 B2
(45) Date of Patent: *Nov. 11, 2014

(54) STABILIZED AGGREGATES OF SMALL CRYSTALLITES OF ZEOLITE Y

(75) Inventors: Wenyih Frank Lai, Bridgewater, NJ (US); Robert E. Kay, Easton, PA (US); Jason Wu, Clinton, NJ (US); Kun Wang, Bridgewater, NJ (US); Robert C. Lemon, Easton, PA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 180 days.

This patent is subject to a terminal disclaimer.

(21) Appl. No.: 13/412,812

(22) Filed: Mar. 6, 2012

(65) Prior Publication Data

US 2013/0029832 A1 Jan. 31, 2013

Related U.S. Application Data

(63) Continuation-in-part of application No. 13/041,597, filed on Mar. 7, 2011, now Pat. No. 8,852,326.

(60) Provisional application No. 61/512,067, filed on Jul. 27, 2011.

(51) Int. Cl.
| | | |
|---|---|---|
| *B01J 29/08* | (2006.01) | |
| *B01J 29/06* | (2006.01) | |
| *B01J 29/10* | (2006.01) | |
| *B01J 29/12* | (2006.01) | |
| *C10G 35/095* | (2006.01) | |
| *C10G 35/06* | (2006.01) | |
| *C10G 35/04* | (2006.01) | |

(52) U.S. Cl.
USPC ............... 208/133; 502/60; 502/64; 502/66; 502/71; 502/79; 208/46; 208/134; 423/700; 423/716

(58) Field of Classification Search
USPC .............. 208/46, 106, 108, 109, 110, 111.01, 208/111.25, 133, 134; 502/60, 64, 66, 71, 502/79; 585/648, 653; 423/700, 716
See application file for complete search history.

(56) References Cited

U.S. PATENT DOCUMENTS

| | | |
|---|---|---|
| 3,293,192 A | 12/1966 | Maher et al. |
| 3,343,913 A | 9/1967 | Robson |

(Continued)

FOREIGN PATENT DOCUMENTS

| | | |
|---|---|---|
| GB | 1058188 | 2/1967 |
| GB | 1061847 | 3/1967 |

(Continued)

OTHER PUBLICATIONS

Shiralkar, et al., Thermal and Structrual Properties of Rare Earth Exchanges Zeolites, 1982, Journal of Thermal Analysis, vol. 25, pp. 399-407.*

(Continued)

*Primary Examiner* — Walter D Griffin
*Assistant Examiner* — Derek Mueller
(74) *Attorney, Agent, or Firm* — Chad A. Guice

(57) ABSTRACT

This invention relates to stabilized aggregates of small primary crystallites of zeolite Y that are clustered into larger secondary particles. At least 80% of the secondary particles may comprise at least 5 primary crystallites. The size of the primary crystallites may be at most about 0.5 micron, or at most about 0.3 micron, and the size of the secondary particles may be at least about 0.8 micron, or at least about 1.0 μm. The silica to alumina ratio of the resulting stabilized aggregated Y zeolite may be 4:1 or more.

32 Claims, 9 Drawing Sheets

(56) References Cited

U.S. PATENT DOCUMENTS

| | | |
|---|---|---|
| 3,354,078 A | 11/1967 | Miale et al. |
| 3,402,996 A | 9/1968 | Maher et al. |
| 3,442,795 A | 5/1969 | Kerr et al. |
| 3,493,519 A | 2/1970 | Kerr et al. |
| 3,506,400 A | 4/1970 | Eberly, Jr. et al. |
| 3,516,786 A | 6/1970 | Maher et al. |
| 3,591,488 A | 7/1971 | Eberly, Jr. et al. |
| 3,640,681 A | 2/1972 | Pickert |
| 3,690,823 A | 9/1972 | Young |
| 3,691,099 A | 9/1972 | Young |
| 3,808,326 A | 4/1974 | McDaniel et al. |
| 3,836,561 A | 9/1974 | Young |
| 3,864,282 A | 2/1975 | Young |
| 3,937,791 A | 2/1976 | Garwood et al. |
| 4,093,560 A | 6/1978 | Kerr et al. |
| 4,218,307 A | 8/1980 | McDaniel |
| 4,273,753 A | 6/1981 | Chang |
| 4,486,296 A * | 12/1984 | Oleck et al. ............ 208/111.15 |
| 5,531,808 A | 7/1996 | Ojo et al. |
| 5,620,590 A | 4/1997 | Absil et al. |
| 5,849,258 A | 12/1998 | Lujano et al. |
| 5,902,564 A | 5/1999 | Lujano et al. |
| 5,993,773 A | 11/1999 | Funakoshi et al. |
| 6,284,218 B1 | 9/2001 | Kuvettu et al. |
| 6,306,363 B1 | 10/2001 | Funakoshi et al. |
| 6,746,659 B2 | 6/2004 | Pinnavaia et al. |
| 2003/0044350 A1 | 3/2003 | Lam et al. |
| 2004/0138051 A1 | 7/2004 | Shan et al. |
| 2005/0239634 A1 | 10/2005 | Ying et al. |
| 2006/0175231 A1 * | 8/2006 | Hansen et al. ............ 208/120.01 |
| 2007/0244347 A1 | 10/2007 | Ying et al. |
| 2008/0138274 A1 | 6/2008 | Garcia-Martinez |
| 2008/0214882 A1 | 9/2008 | Pinnavaia et al. |
| 2009/0029847 A1 | 1/2009 | Euzen et al. |
| 2009/0090657 A1 | 4/2009 | Ying et al. |
| 2010/0147747 A1 | 6/2010 | Elia et al. |

FOREIGN PATENT DOCUMENTS

| | | |
|---|---|---|
| JP | 53101003 | 9/1978 |
| NL | 7604264 | 4/1976 |

OTHER PUBLICATIONS

G.T. Kerr, "Hydrogen Zeolite Y, Ultrastable Zeolite Y, and Aluminum-Deficient Zeolites"—Chapter 19 in W. Meier, et al. Advances in Chemistry, American Chemical Society, Washington, DC, 1973.

Letter to the Editors, "Superactive Crystalline Aluminosilicate Hydrocarbon Catalysts", Journal of Catalysis, 4, 1965, pp. 527-529.

H. Julide Koroglu, et al., "Effects of low-temperature gel aging on the synthesis of zeolite Y at different alkalinities", Journal of Crystal Growth, 241, 2002, pp. 481-488.

C. Berger, et al., "The synthesis of large crystals of zeolite Y revisited", Microporous and Mesoporous Materials, 83, 2005, pp. 333-344.

J. N. Miale, et al., "Catalysis by Crystalline Aluminosilicates IV. Attainable Catalytic Cracking Rate Constants, and Superactivity", Journal of Catalysis, 6, 1966, pp. 278-287.

2510740, DW, Sep. 30, 1976, BASF AG.

C. T. Campbell, et al., "The Adsorption, Desorption, and Reactions of CO and O2 on Rh2", Journal of Catalysis, 54, 1978, pp. 289-302.

K. Rajagopalan, et al., "Influence of Zeolite Particle Size on Selectivity During Fluid Catalytic Cracking", Applied Catalysis, 23, 1986, pp. 69-80.

D. H. Olson, et al., "Chemical and Physical Properties of the ZSM-5 Substitutional Series", Journal of Catalysis, 61, 1980, pp. 390-396.

Shigeo Miwa, editor, "Powder Engineering Theory", 1981, Nikkan Kogyo Shinbun KK, pp. 1-31.

* cited by examiner

STABILIZED AGGREGATES OF SMALL CRYSTALLITES OF ZEOLITE Y

CROSS-REFERENCE TO RELATED APPLICATION

This application is a continuation-in-part of U.S. Non-Provisional Application Ser. No. 13/041,597 filed Mar. 7, 2011 and claims priority to U.S. Provisional Application Serial No. 61/512,067 filed Jul. 27, 2011, which are herein incorporated by reference in their entirety.

FIELD

This invention relates to stabilized aggregates of small crystallites of zeolite Y. Small primary crystallites of zeolite Y can cluster into larger secondary particles, at least 80% of which may comprise at least 5 primary crystallites. When the outer surfaces of the secondary particles are viewed, e.g., in a SEM image, the average size (width/diameter) of the primary crystallites may be about 0.5 µm or less, or about 0.3 micron or less, though the average size of the secondary particles may be about 0.8 µm or more, or about 1.0 µm or more. The silica to alumina ratio of the resulting stabilize zeolite Y products may be 4:1 or more. Methods for stabilizing the aggregates of Y crystals are also disclosed. The stabilized aggregates may be used as sorbents, catalysts, and/or catalyst supports.

BACKGROUND

Zeolite Y, a member of the Faujasite family, is widely used in many catalytic processes such as fluid catalytic cracking (FCC), hydrocracking, aromatics alkylation, and aromatics transalkylation. A particular type of zeolite Y is known as ultra-stable Y zeolite (USY). Typical USY has crystal morphology of non-aggregated and submicrosized crystals and may contain intra-crystal mesopores after post-treatment involving high temperature steaming. The individual submicrosized crystals may have crystal defects which produce variously oriented crystal grains within an individual crystal particle. U.S. Pat. No. 6,284,218 states that such defects include stacking faults and screw defects.

When heavy molecules are catalytically processed, such as in catalytic cracking of heavy gas oil, transport properties (both intra-particle and inter-particle) of the catalyst are important, in order to operate outside of the diffusion limited regime that often leads to coking.

The article by K. Rajagopalan et al., "Influence of Zeolite Particle Size on Selectivity During Fluid Catalytic Cracking", *Applied Catalysis*, 1986, 23, 69-80, reports that smaller particle size NaY zeolite fluid catalytic cracking (FCC) catalysts exhibited improved activity and selectivity to intermediate cracked products, such as gasoline and light cycle oil. Selectivity differences were said to be explained by considering the effect of diffusion resistance on the rate constants for cracking of gas oil and gasoline.

U.S. Pat. No. 5,620,590 reports that small crystal zeolite Y of less than 1 micron shows activity benefit in hydrocracking compared to larger crystals. However, small crystal zeolites often present problems in manufacturing (e.g., difficulties in filtration and formulation) due to their small particle sizes and low bulk density. Therefore, it is desirable to have zeolites that possess the performance advantages of small particles, while still maintaining the easy processability of large particles. Thus, one ideal zeolite morphology includes large secondary particles (often greater than 1 micron) formed by agglomeration of smaller primary crystallites (often less than, or even much less than, 1 micron). Furthermore, to improve mass transportation rates, zeolite crystals with small size or aggregated crystals containing inter-crystal mesopores can be desirable, e.g., for reducing diffusion limitations.

Conventional zeolite Y tends to have a crystal or primary crystallite size of much greater than 0.1 µm, even greater than 1 µm. Examples of such conventional forms of zeolite Y include U.S. Pat. Nos. 3,343,913, 3,690,823, and 3,808,326, for example.

Small crystal size zeolite Y may be prepared by methods disclosed in U.S. Pat. Nos. 3,516,786 and 3,864,282.

Zeolite X, zeolite Y, and natural faujasite have identical structure types and differ only in the ratio of silica to alumina in the final crystal structure. For example, zeolite X is generally referred to as having an $Si/Al_2$ molar ratio of 2-3, whereas zeolite Y is generally referred to as having an $Si/Al_2$ molar ratio of 3-7.

U.S. Pat. Nos. 5,993,773 and 6,306,363 describe various forms of low-silica faujasite zeolite, referred to as LSX, having silica to alumina molar ratios of 1.9-2.1. These patents include SEM photographs showing LSX zeolite particle size and morphology.

In U.S. Pat. No. 6,306,363, it is stated that, when zeolites are observed by a SEM, they may be visible either (1) in the form of non-aggregated primary crystallites only, which are the smallest units of zeolite particles, or (2) in the form of secondary particles which are formed by agglomeration of a plurality of primary crystallites. Primary crystallites of zeolites may have their shapes predetermined, depending upon the type of zeolite. For example, A-type zeolite tends to have a cubic shape, and faujasite-type zeolite tends to have an octahedral shape or a polyhedral shape developed from a generally spherical shape with some angularity, as shown in FIG. 3 of this patent. However, it is possible for faujasite-type zeolites to have other shapes, such as elongated shapes (e.g., rod-like shapes).

Usually, particle sizes distributions of these particles are roughly symmetric about an average peak maximum. A method for obtaining an average particle size from particles having a distribution is described in detail, for example, at pages 1 to 31 of "Powder Engineering Theory", Shigeo Miwa ed., 1981, Nikkan Kogyo Shinbun K.K. The primary crystallite size of the faujasite-type zeolite may be described as a number average particle size of the primary crystallite particle diameters (observed by SEM) as approximated to spheres, which is called the "projected area diameter" or "Heywood diameter".

LSX in U.S. Pat. No. 6,306,363 is described as being of high purity and characterized in its primary crystallite size of at least 0.05 µm and less than 1 µm, which is said to be a fine (small) size, in comparison with previously known forms of LSX, e.g., where the primary crystallite size is from 3-5 µm, and even more generally where it is at least 1 µm. In this patent, it is stated that, when fine LSX of high purity is used, for example, as an adsorbent of various substances, diffusion into the interior will be facilitated, and improvement in various dynamic properties can be expected.

The LSX described in U.S. Pat. No. 5,993,773 is said to be characterized not only by high purity, but also a peculiar primary crystallite size distribution, wherein the primary crystallite size of a smaller set of particles is from 1-8 µm, the primary crystallite size of a larger set of particles is from 5-15 µm, and 90% or more of the particles are in the smaller set. The right hand portion of FIG. 2 of this patent illustrates a large single crystal or primary crystallite having a spherical polyhedral shape with angularity or edges developed.

SUMMARY

A stabilized aggregated form of zeolite Y comprises small primary crystallites and secondary particles of larger size. At least 80%, e.g., at least 90% or at least 95%, of the primary crystallites may be aggregated or clustered to form the secondary particles. The ratio of the average size (width/diameter) of the secondary particles to the average size (width/diameter) of the primary crystallites, when the outer (i.e., external) surfaces of the secondary particles are viewed, may be at least 3:1, for example at least 5:1 or at least 10:1. When the outer surfaces of the secondary particles are viewed, e.g., in an SEM image, the average size of the primary crystallites in a secondary particle may be about 0.5 µm or less, for example about 0.3 µm or less, about 0.2 µm or less, or about 0.1 µm or less, whereas the average size of the secondary particles may be about 0.8 µm or more, for example about 1.0 µm or more or about 2.0 µm or more. At least 80%, e.g., at least 90% or at least 95%, of the aggregated secondary particles may comprise at least 5, for example at least 10, primary crystallites. These primary crystallites and secondary particles as described herein may be observable, e.g., by an SEM under sufficient conditions including appropriate magnification and resolution.

The average sizes of the primary crystallites and secondary particles can be determined, for instance, by viewing one or more sufficient two-dimensional SEM images of the secondary particles and approximating the shape of the primary crystallites and secondary particles roughly as two-dimensional spherical projections (circles). When percentages (e.g., 80%, 90%, 95%, or the like) of primary crystallites and secondary particles are referred to herein, it should be understood that these percentages are based on numbers of these particles. Although SEM images referred to herein do not necessarily depict all of the particles in an entire batch of primary crystallites and secondary particles, it should also be understood that the SEM images referred to herein are viewed as representative of an entire batch of primary crystallites and secondary particles, including even those particles not specifically observed.

The aggregates of zeolite Y of the present invention can have enhanced stability, particularly enhanced thermal and/or hydrothermal stability, relative to the as-synthesized forms of these aggregates. The present stabilized aggregates of zeolite Y, which can advantageously have an alkali metal content less than 4 wt % and/or a rare earth metal content of at least 2 wt %, can further have different chemical compositions than the as-synthesized forms of these aggregates, which can typically comprise as much as 8 wt % or more alkali metal content and essentially no rare earth metals.

Thus, without being bound by theory, it is believed that the chemical composition change may be a reason for the increased stability. As such, aggregates of zeolite Y may attain increased stability through one or more of the following treatments: by exchanging alkali metal (e.g., sodium) atoms from the as-synthesized form of the aggregates with an ammonium salt and by calcining the ammonium exchanged aggregates under conditions sufficient to decompose ammonium; by steaming the calcined, ammonium exchanged form of the aggregates under steaming conditions sufficient, e.g., to remove framework aluminum from the zeolite Y crystallites; by contacting (washing) steamed aggregates with an aqueous acid, e.g., to remove non-framework aluminum from the zeolite Y aggregates; and by incorporating rare earth metal atoms into the aggregates by an ion exchange process, e.g., to attain at least about 2 wt % rare earth content in the zeolite Y aggregates.

The stabilized aggregates may optionally be further formulated for use as an organic conversion catalyst for processes such as dewaxing, fluid catalytic cracking, and/or hydrocracking.

DETAILED DESCRIPTION OF THE EMBODIMENTS

Figure 1B:
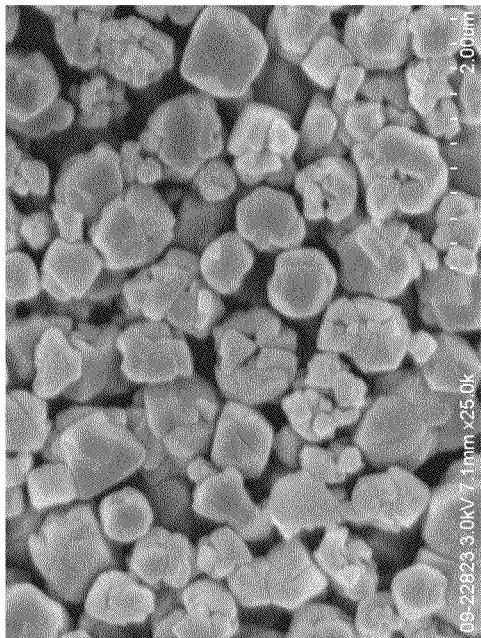
FIGS. 1A & 1B show scanning electron microscope (SEM) images of comparative non-aggregated NaY samples prepared according to Examples 1A & 1B.

Smaller crystallites of zeolite Y can be clustered into discrete, larger particle size bodies. The smaller particle size crystallites are also referred to herein as primary crystallites or primary particles. The clusters of these primary crystallites are also referred to herein as secondary particles, aggregates, and/or agglomerates. In certain cases herein, the zeolite Y can alternately be described as Mesoporous-Y (Meso-Y).

The secondary particles may be essentially uniform in size. For instance, at least 80%, e.g., at least 90% or at least 95%, of the sizes of the secondary particles may vary on average by no more than ~0.5 micron, for example no more than ~0.3 micron or no more than micron, as observed by SEM, measuring average diameters as approximated using spherical secondary particulate shapes.

As indicated by the spherical approximations for size (width/diameter) determinations, the secondary particles may be essentially spherical in shape. For instance, at least 80%, e.g., at least 90% or at least 95%, of the secondary particles may have an aspect ratio of between 0.7 and 1, for example, between 0.8 and 1. Aspect ratio may be calculated by dividing the shortest cross-sectional dimension of a secondary particle by the longest cross-sectional dimension of the secondary particle, as observed by SEM. The secondary particles may appear as clusters of primary particles, having a broccoli-like morphology/appearance.

The primary crystallites may have a non-spherical shape. For example, the primary crystallites may have a smooth or roughened octahedral shape, which is more or less typical of certain faujasite type zeolite crystals. However, the primary crystallites may have other less common shapes, such as elongated or rod-like shapes:

When secondary particles are viewed, for example using SEM techniques, only the exterior surfaces or shells of the secondary particles are typically visible. Consequently, the entire crystal morphology of the primary crystallites, as well as of the interior of the secondary particles, is not usually observed visually. Accordingly, the secondary particles of the present invention may possess or lack primary crystallites in the interior regions of the secondary particles, which cannot be observed by SEM. Additionally or alternatively, some or all of the primary crystallites may or may not be elongated along an axis extending from the center of the secondary particles to the center of the surface of each crystallite, as observed using SEM.

In aggregates of individual primary crystallites, spaces can exist among individual primary crystallites, thus providing pore spaces, especially mesopores. In contrast, stacking faults within an individual crystallite tend not to provide pore spaces. One or more stacking faults may exist within any individual primary crystallite.

The secondary particles may possess an external surface area of about 10 m$^2$/g or more, for example, about 20 m$^2$/g or more or about 40 m$^2$/g or more, especially after undergoing calcination and/or steaming. Conventional forms of zeolite Y, such as those having non-aggregated primary crystallites with a size of 1 micron or more, tend to have an external surface area of less than 10 m$^2$/g. The relatively high external surface area of the secondary particles can be an indication generally of porous gaps between individual primary crystallites, and specifically of mesopores in the internal regions of the secondary particles. A single crystal of comparable size in the form of a generally spherical shape (with angularity or edges developed) would be expected to have a smaller external surface area.

The centers of the secondary particles may, in certain cases, be less dense than the edges of the secondary particles, as measured by SEM or TEM. This lack of density in the centers of the secondary particles can be a further indication that these secondary particles are indeed an aggregation of primary crystallites, rather than a single large crystal.

Elemental mapping of secondary particles may reveal that the Si/Al ratio can be relatively uniform throughout the secondary particles. Such a uniform Si/Al ratio can provide further indication that these secondary particles are indeed an aggregation of primary crystallites, rather than a single large crystal or large particles with an aluminum-, or a silicon-, rich (amorphous) core.

The zeolite Y in the aggregates may have a silica to alumina (Si/Al$_2$) ratio of at least 4 (i.e., at least 4:1), for example of at least 4.5, of at least 5, or from 5 to 6.

The aggregates of zeolite Y may be combined with one or more metal oxide binders (optional) and at least one hydrogenating metal component, in order to form a catalyst suitable for hydrocracking and/or dewaxing. Examples of such hydrogenating metal components can include one or more noble metals or one or more non-noble metals. Suitable noble metals imparting hydrocracking/dewaxing catalyst functionality can include platinum, palladium, and/or other noble metals from Groups 8-10 of the Periodic Table, such as iridium and/or rhodium. Suitable non-noble metals imparting hydrocracking/dewaxing catalyst functionality can include those of Groups 5-7 of the Periodic Table. The Periodic Table used in this specification is the table approved by IUPAC and the U.S. National Bureau of Standards, as shown for instance in the table of the Fisher Scientific Company, Catalog No. 5-702-10. Preferred non-noble metals can include chromium, molybdenum, tungsten, cobalt, nickel, and combinations thereof, such as cobalt-molybdenum, nickel-molybdenum, nickel-tungsten, cobalt-tungsten, cobalt-nickel-molybdenum, cobalt-nickel-tungsten, nickel-molybdenum-tungsten, and cobalt-molybdenum-tungsten. Non-noble metal components may be pre-sulfided prior to use by exposure to a sulfur-containing gas (such as hydrogen sulfide) or liquid (such as a sulfur-containing hydrocarbon stream, e.g., derived from crude oil and/or spiked with an appropriate organosulfur compound) at an elevated temperature to convert the oxide form to the corresponding sulfide form of the metal. The catalyst may additionally or alternately be combined with a binder material and used in hydrocracking processes, such as described in U.S. Pat. No. 5,620,590.

In preferred embodiments of the catalysts herein, the aggregates of zeolite Y (Meso-Y) are combined with at least one metal oxide binder (as described prior) and further with at least one hydrogenating metal component, in order to form a final hydrocarbon processing catalyst. Examples of such hydrogenating metal components can include one or more noble metals or one or more non-noble metals.

The aggregates of zeolite Y, binder and additional components may be extruded, spray-dried, or otherwise shaped into a catalyst particle for use in hydroconversion processes described herein. In preferred embodiments of the catalysts herein, the final catalyst contains an active Group 5-7 and/or Group 8-10 metal. In a preferred embodiment, the catalyst is comprised of at least one Group 5-7 metal selected from Mo and W, and at least one Group 8-10 metal selected from Ni and Co. In another preferred embodiment, the catalyst is comprised of at least one Group 8-10 metal selected from Pt and Pd (noble metals). In a preferred embodiment, the Group 5-7 metal is Mo and the Group 8-10 metal is Co. In another preferred embodiment, the catalyst is comprised of Pt. The active Group 5-7 or Group 8-10 metals may be incorporated into the catalyst by any technique known in the art. A preferred technique for active metal incorporation into the catalyst herein is the incipient wetness technique.

The amount of hydrogenation metal in the catalyst can be at least 0.1 wt % based on catalyst, or at least 0.15 wt %, or at least 0.2 wt %, or at least 0.25 wt %, or at least 0.3 wt %, or at least 0.5 wt % based on the catalyst. For embodiments where the Group 8-10 metal is Pt, Pd, or a combination thereof, the amount of metal is preferably from 0.1 to 5 wt %, more preferably from 0.2 to 4 wt %, and even more preferably from 0.25 to 3.5 wt %. For embodiments where the metal is a combination of a Group 8-10 non-noble metal with a Group 5-7 metal, the combined amount of metal is preferably from 0.25 wt % to 40 wt %, more preferably from 0.3 wt % to 35 wt %, and even more preferably from 1 wt % to 25 wt %.

The aggregated form of zeolite Y may have a mesopore volume of at least 0.025 cm$^3$/gram (abbreviated cc/g herein), particularly in the inter-crystalline regions of the aggregates. Non-aggregated forms of zeolite Y thus tend to lack mesopores (which are defined herein as pores having a diameter from about 20 to about 300 Angstroms). The unit cell size (UCS) of the zeolite Y can be 25 Angstroms or less, e.g., between 24 and 25 Angstroms.

Small size zeolite Y can be prepared using a reaction mixture containing a source of alumina, a source of silica, a source of sodium ions, a source of water, and optionally a source of hydroxyl ions. Although the reaction mixture is described as containing sources of alumina and silica, it should be understood that these are actually sources of aluminum atoms and silicon atoms, respectively. Nevertheless, since the zeolite Y structure is usually described in terms of oxidized versions of these atoms, and indeed to facilitate the standard characterization of such zeolitic structures with respect to ratios of silica to alumina, and the like, the sources are referred to herein for convenience in their oxidized forms.

Sources of alumina for preparing aggregates of small size zeolite Y can be in the form of a soluble salt, for example a sodium salt of alumina such as commercially available from US Aluminate. Other suitable alumina sources can additionally or alternately include other aluminum salts, such as the chloride, aluminum alcoholates, hydrated aluminas such as gamma alumina, pseudoboehmite, and colloidal alumina, and the like, and combinations thereof.

The silica source for preparing aggregates of small size zeolite Y can be a precipitated silica, such as Ultrasil®, which is commercially available from Evonik Degussa. Other suitable silica sources can additionally or alternately include powdered silica (including precipitated silica, such as Ultrasil PM Modified® and/or Zeosil®, as well as silica gels), silicic acid, colloidal silica (such as Ludox®), dissolved silica, and the like, and combinations thereof. In the presence of a base, certain silica sources may form silicates. According to certain particular embodiments exemplified herein, a sodium silicate solution can further additionally or alternately be used as a source of silica. Still further additionally or alternately, a precipitated silica (particularly Ultrasil PM Modified®, Ultrasil®, and/or Sipemat®) can be used as a source of silica. Especially in, but not limited to, situations where a precipitated silica is used as a preferred source of silica, the reaction mixture for forming the aggregates of small size zeolite Y can comprise one or more of a Si/Al$_2$ molar ratio of about 10 or more, an H$_2$O/Si molar ratio of about 15 or less, and an OH$^-$/Si molar ratio of about 0.85 or less. Additionally or alternately, the reaction mixture for forming the aggregates of small size zeolite Y may comprise one or more of a silica to alumina molar ratio from about 10 to about 20, an H$_2$O/SiO$_2$ molar ratio from about 10 to about 20, when hydroxyl ion sources are present an OH$^-$/SiO$_2$ molar ratio from about 0.5 to about 1.0, and a Na$^+$/SiO$_2$ molar ratio from about 0.5 to about 1.0.

The thermal and hydrothermal stability of the aggregates of zeolite Y can be improved by removal of aluminum from the aggregates, by steaming, and/or by exchanging cations in the aggregates with yttrium and/or rare earth metal ions, typically lanthanides (i.e., La, Ce, Pr, Nd, Pm, Sm, Eu, Gd, Tb, Dy, Ho, Er, Tm, Yb, and Lu), particularly including lanthanum and/or cerium.

These rare earth metal ions can typically be utilized in the form of suitable precursors, e.g., inorganic salts such as sulfates, nitrates (e.g., trinitrates such as La(NO$_3$)$_3$ and Ce(NO$_3$)$_3$), oxides, halides (e.g., chlorides), and mixtures thereof. The ion exchange can be conducted in aqueous and/or non-aqueous medium, which can include water, methanol, ethanol, and the like, as well as mixtures thereof. The ion exchange can be conducted at any suitable temperature, such as at room temperature (about 20-25° C.) or from about 10° C. to about 90° C. The ion exchange process can be done in a single step or over multiple steps, in order to achieve a desired rare earth metal content.

Forms of the present aggregates of zeolite Y, such as the as-synthesized forms, may be subjected to various treatments to remove structural aluminum therefrom. Many of these techniques rely upon the removal of aluminum from the structural framework of the zeolite by chemical agents appropriate to this end. A considerable amount of work on the preparation of aluminum-deficient faujasites has been performed and is reviewed in Advances in Chemistry Series No. 121, Molecular Sieves, G. T. Kerr, American Chemical Society, 1973. Specific methods for preparing dealuminized zeolites are described in the following, and reference is made to them for details of the method, which are hereby incorporated by reference herein: Catalysis by Zeolites ((International Symposium on Zeolites, Lyon, Sep. 9-11, 1980), Elsevier Scientific Publishing Co., Amsterdam, 1980 (dealuminization of zeolite Y with silicon tetrachloride); U.S. Pat. No. 3,442,795 and Great Britain U.S. Pat. No. 1,058,188 (hydrolysis and removal of aluminum by chelation); Great Britain U.S. Pat. No. 1,061,847 (acid extraction of aluminum); U.S. Pat. No. 3,493,519 (aluminum removal by steaming and chelation); U.S. Pat. No. 3,591,488 (aluminum removal by steaming); U.S. Pat. No. 4,273,753 (dealuminization by silicon halide and oxyhalides); U.S. Pat. No. 3,691,099 (aluminum extraction with acid); U.S. Pat. No. 4,093,560 (dealuminization by treatment with salts); U.S. Pat. No. 3,937,791 (aluminum removal with Cr(III) solutions); U.S. Pat. No. 3,506,400 (steaming followed by chelation); U.S. Pat. No. 3,640,681 (extraction of aluminum with acetylacetonate followed by dehydroxylation); U.S. Pat. No. 3,836,561 (removal of aluminum with acid); German Patent No. 2,510,740 (treatment of zeolite with chlorine or chlorine-contrary gases at high temperatures), Netherlands Patent No. 7,604,264 (acid extraction), Japanese Publication No. 53,101,003 A (treatment with EDTA or other materials to remove aluminum); and *J. Catalysis*, 54, 295 (1978) (hydrothermal treatment followed by acid extraction), inter alia.

Highly siliceous forms of zeolite Y may be prepared by steaming and/or by acid extraction of structural aluminum, but, because zeolite Y in its usual as-synthesized condition tends to be relatively unstable to acid, it must first be converted to an acid-stable form. Methods for doing this are known, and one of the most common forms of acid-resistant zeolite Y is known as "Ultrastable Y" (USY), e.g., as described in U.S. Pat. Nos. 3,293,192 and 3,402,996 and in Society of Chemical Engineering (London) Monograph Molecular Sieves, page 186 (1968), by C. V. McDaniel and P. K. Maher, each of which are hereby incorporated by reference herein for details of the zeolite and preparation. In general, "ultrastable" refers to Y-type zeolite that is highly resistant to degradation of crystallinity by high temperature and steam treatment and that can be characterized by an R$_2$O content (wherein R is Na, K, or any other Group 1 metal ion) of less than 4 wt % (for example less than 2 wt %, preferably less than 1 wt %), a unit cell size less than 24.5 Angstroms or less than 24.6 Angstroms, and a silica to alumina mole ratio in the range of 3.5-7 or higher. The ultrastable form of Y-type zeolite can be obtained primarily by a substantial reduction of the alkali metal (Group 1) ion content and of the unit cell size.

The ultrastable zeolite Y can be identified both by the smaller unit cell and the low alkali metal content in the crystal structure.

In certain embodiments, the ultrastable form of the Y-type zeolite can be prepared by successively base exchanging a Y-type zeolite with an aqueous solution of an ammonium salt, such as ammonium nitrate, until the alkali metal content of the Y-type zeolite is reduced to less than 4 wt %. The base exchanged zeolite can then be calcined at appropriate conditions (e.g., at a temperature from about 540° C. to about 800° C. for up to several hours), cooled, and successively base exchanged again with an aqueous solution of an ammonium salt until the alkali metal content is reduced to less than ~1 wt % (e.g., less than ~0.5 wt %), which can be followed by washing and calcination again at appropriate conditions to produce an ultrastable zeolite Y. The sequence of ion exchange and heat treatment can result in the substantial reduction of the alkali metal content of the original zeolite and can also advantageously result in a unit cell shrinkage, which is believed to lead to the rather high stability of the resulting Y-type zeolite.

The ultrastable zeolite Y may then be extracted, e.g., with acid, to produce a highly siliceous form of the zeolite. Methods for increasing the silica to alumina ratio of zeolite Y by acid extraction are described, e.g., in U.S. Pat. Nos. 4,218,307, 3,591,488, and 3,691,099, which are each incorporated herein by reference for details of these methods.

As in the case of many catalysts, it may be desirable to incorporate the present aggregates of zeolite Y with another material, e.g., to impart resistance to the temperatures and other conditions employed in organic conversion processes. Such materials include active and inactive materials, synthetic and/or naturally-occurring zeolites, inorganic materials (such as clays, silica, and/or metal oxides such as alumina), and the like, as well as combinations thereof. The inorganic materials may be either naturally occurring or synthesized by manipulating a precursor form, such as a gelatinous precipitate and/or gel (including mixtures of silica and metal oxides). Use of an active material in conjunction with the molecular sieve produced by the present process (i.e., combined therewith after sieve formation and/or present during sieve synthesis) can tend to change the conversion and/or selectivity of the catalyst in certain organic conversion processes. Inactive materials can suitably serve as diluents, e.g., to control the amount of conversion and/or any undesirable effects of conversion in a given process, so that products can be obtained economically and orderly without employing other means for controlling the rate of reaction. These other materials may be incorporated into naturally-occurring clays (e.g., bentonite, kaolin, or the like, or combinations thereof), e.g., to improve the crush strength of the catalyst under commercial operating conditions. Said materials (i.e., clays, oxides, etc.) can additionally or alternately function as catalyst binders. It can be desirable to provide a catalyst having good crush strength, in order to prevent the catalyst from breaking down into powder-like materials in commercial use. These binder materials have been employed normally only for the purpose of improving the crush strength of the catalyst.

Naturally-occurring clays that can be composited with molecular sieve produced by the present process can include, but are not limited to, the montmorillonite and kaolin families, which include the subbentonites and those kaolins commonly known as Dixie, McNamee, Georgia, and/or Florida clays, as well as others in which the main mineral constituent is halloysite, kaolinite, dickite, nacrite, and/or anauxite. Such clays can be used in the raw state, as originally mined or initially subjected to calcination, acid treatment, and/or chemical modification. Binders useful for compositing with molecular can additionally or alternately include inorganic oxides such as silica, zirconia, titania, magnesia, beryllia, alumina, and mixtures thereof.

Additionally or alternately, the aggregated zeolite Y can be composited with a porous matrix material, such as silica-alumina, silica-magnesia, silica-zirconia, silica-thoria, silica-beryllia, silica-titania, ternary compositions (such as silica-alumina-thoria, silica-alumina-zirconia silica-alumina-magnesia, and silica-magnesia-zirconia), and the like, e.g., by extrusion or spray drying methods.

When present, the relative proportions of finely divided crystalline molecular sieve material and binder/matrix component can vary widely, with the zeolite/molecular sieve content ranging from about 1 wt % to about 90 wt %, and more usually, particularly when the composite is prepared in the form of beads, powders, or extrudates, in the range from about 2 wt % to about 80 wt % of the composite. In typical embodiments employing binder, the zeolite/molecular sieve component can be at least 10 wt % of the composite, for example at least 20 wt % or at least 30 wt %.

The rare earth metal content of a composite/catalyst composition according to the present invention can be at least about 0.5 wt % (such as from about 0.5 wt % to about 10 wt %), for example at least about 1 wt %, at least about 2 wt %, from about 1 wt % to about 10 wt %, or from about 2 wt % to about 5 wt %, based on the weight of the composite/catalyst composition. Additionally or alternately, relative to the weight of the zeolite Y component only, the rare earth metal content can be at least about 1 wt % (such as from about 1 wt % to about 20 wt %), for example at least about 2 wt %, at least about 4 wt %, from about 2 wt % to about 20 wt %, or from about 4 wt % to about 10 wt %, based on the weight of the zeolite Y component only, which value can depend heavily on whether any, and/or how much, binder and/or matrix material is composited with the zeolite Y aggregates in a formulated catalyst composition.

The rare earth component can suitably be incorporated into the zeolite Y component by ion exchange into/onto the zeolite Y component, through any one or more of the unbound/unmatrixed primary crystal form, the unbound/unmatrixed aggregated crystal form, and the bound/matrixed aggregated composite/catalyst form. The rare earth metal ions may be incorporated into/onto the zeolite Y (for example, by ion exchange), which, before rare earth stabilization, can exhibit a unit cell size from about 24.45 Angstroms to about 24.65 Angstroms) followed by additional steaming and/or calcination steps to lower the unit cell size of the zeolite Y (for example, to a range from about 24.20 Angstroms to about 24.50 Angstroms). The zeolite Y should have a relatively low alkali metal (e.g., sodium) content in order to impart stability, as well as to impart satisfactory cracking activity; this can typically be attained by ammonium exchange performed during the stabilization process to reach a desirably low alkali metal (e.g., sodium) level, for example not more than ~1 wt % or not more than ~0.5 wt %, based on the weight of zeolite Y component (for stability) and/or based on the weight of the entire catalyst composition (for cracking activity).

When metal elements (including rare earths and other metals, as applicable) are incorporated into/onto a zeolite Y-containing catalyst composition according to the invention, they can preferably be present within the interior pore structure and/or framework of the zeolite Y crystallites. For instance, a cracking catalyst containing an aggregated zeolite Y to which a rare earth metal has been added may be re-calcined to ensure relatively low unit cell size and stability, and then a non-rare earth metal atom may be incorporated (e.g., by ion exchange and/or by impregnation under conditions which permit cation exchange to take place) into/onto the zeolite, so that the metal(s) is (are) immobilized, e.g., at least partially and preferably predominantly within the pore structure and/or framework, as applicable.

Catalyst compositions comprising aggregates of small crystal size zeolite Y, as described herein, may be used to catalyze a wide variety of organic/hydrocarbon chemical conversion processes, including many of present commercial/industrial importance. Examples of chemical conversion processes which can be effectively catalyzed by such catalyst compositions, by themselves and/or in combination with one or more other catalytically active substances (including other crystalline catalysts), include those requiring a catalyst with acid activity. Specific examples of such catalytic processes can include, but are not necessarily limited to:

(a) alkylation of aromatics with short chain ($C_2$-$C_6$) olefins, e.g., alkylation of ethylene or propylene with benzene to produce ethylbenzene or cumene respectively, in the gas or liquid phase, with reaction conditions optionally including one or more of a temperature from about 10° C. to about 250° C., a pressure from about 0 psig to about 500 psig (about 3.5 MPag), a total weight hourly space velocity (WHSV) from about 0.5 $hr^{-1}$ to about 100 $hr^{-1}$, and an aromatic/olefin mole ratio from about 0.1 to about 50;

(b) alkylation of aromatics with long chain ($C_{10}$-$C_{20}$) olefins, in the gas or liquid phase, with reaction conditions optionally including one or more of a temperature from about 250° C. to about 500° C., a pressure from about 0 psig to 500 psig (about 3.5 MPag), a total WHSV from about 0.5 $hr^{-1}$ to about 50 $hr^{-1}$, and an aromatic/olefin mole ratio from about 1 to about 50;

(c) transalkylation of aromatics, in gas or liquid phase, e.g., transalkylation of polyethylbenzenes and/or polyisopropylbenzenes with benzene to produce ethylbenzene and/or cumene respectively, with reaction conditions optionally including one or more of a temperature from about 100° C. to about 500° C., a pressure from about 1 psig (about 7 kPag) to about 500 psig (about 3.5 MPag), and a WHSV from about 1 $hr^{-1}$ to about 10,000 $hr^{-1}$;

(d) disproportionation of alkylaromatics, e.g., disproportionation of toluene to produce xylenes, with reaction conditions optionally including one or more of a temperature from about 200° C. to about 760° C., a pressure from about 1 atm (about 0 psig) to about 60 atm (about 5.9 MPag), a WHSV from about 0.1 $hr^{-1}$ to about 20 $hr^{-1}$, and a hydrogen/hydrocarbon mole ratio from 0 (no added hydrogen) to about 50;

(e) dealkylation of alkylaromatics, e.g., deethylation of ethylbenzene, with reaction conditions optionally including one or more of a temperature from about 200° C. to about 760° C., a pressure from about 1 atm (about 0 psig) to about 60 atm (about 5.9 MPag), a WHSV from about 0.1 $hr^{-1}$ to about 20 $hr^{-1}$, and a hydrogen to hydrocarbon mole ratio from 0 (no added hydrogen) to about 50;

(f) isomerization of alkylaromatics, such as xylenes, with reaction conditions optionally including one or more of a temperature from about 200° C. to about 540° C., a pressure from about 100 kPaa to about 7 MPaa, a WHSV from about 0.1 $hr^{-1}$ to about 50 $hr^{-1}$, and a hydrogen/hydrocarbon mole ratio from 0 (no added hydrogen) to about 10;

(g) reaction of paraffins with aromatics, e.g., to form alkylaromatics and light gases, with reaction conditions optionally including one or more of a temperature from about 260° C. to about 375° C., a pressure from about 0 psig to about 1000 psig (about 6.9 MPag), a WHSV from about 0.5 $hr^{-1}$ to about 10 $hr^{-1}$, and a hydrogen/hydrocarbon mole ratio from 0 (no added hydrogen) to about 10;

(h) paraffin isomerization to provide branched paraffins with reaction conditions optionally including one or more of a temperature from about 200° C. to about 315° C., a pressure from about 100 psig (about 690 kPag) to about 1000 psig (about 6.9 MPag), a WHSV from about 0.5 $hr^{-1}$ to about 10 $hr^{-1}$, and a hydrogen to hydrocarbon mole ratio from about 0.5 to about 10;

(i) alkylation of iso-paraffins, such as isobutane, with olefins, with reaction conditions optionally including one or more of a temperature from about −20° C. to about 350° C., a pressure from about 0 psig to about 700 psig (about 4.9 MPag), and a total olefin WHSV from about 0.02 $hr^{-1}$ to about 10 $hr^{-1}$;

(j) dewaxing of paraffinic feeds with reaction conditions optionally including one or more of a temperature from about 200° C. to about 450° C., a pressure from about 0 psig to about 1000 psig (about 6.9 MPag), a WHSV from about 0.2 $hr^{-1}$ to about 10 $hr^{-1}$, and a hydrogen/hydrocarbon mole ratio from about 0.5 to about 10;

(k) cracking of hydrocarbons with reaction conditions optionally including one or more of a temperature from about 300° C. to about 700° C., a pressure from about 0.1 atm (about 10 kPag) to about 30 atm (about 3 MPag), and a WHSV from about 0.1 $hr^{-1}$ to about 20 $hr^{-1}$; and (l) isomerization of olefins with reaction conditions optionally including one or more of a temperature from about 250° C. to about 750° C., an olefin partial pressure from about 30 kPa to about 300 kPa, and a WHSV from about 0.5 $hr^{-1}$ to about 500 $hr^{-1}$.

Particular organic/hydrocarbon conversion processes, for which catalysts comprising the previously described stabilized aggregates of small crystallite size zeolite Y can be useful, can include processes for dewaxing a waxy-containing hydrocarbon feedstock, such as described in U.S. Patent Application Publication No. 2010/0147747, and/or processes for cracking of hydrocarbons. As is well known in the art, catalytic cracking processes can convert hydrocarbon compounds in a feedstock to product hydrocarbons of lower molecular weight than the feedstock.

For instance, the mesoporous oxide materials according to the present invention may be used in catalytic processes operating at temperatures from about 200° C. to about 870° C. and under reduced, atmospheric, or superatmospheric pressure. The catalytic processes may take place in a fixed bed, moving bed, or fluidized bed, as appropriate to each specific process, and, if moving, the hydrocarbon feedstock flow may be either concurrent or countercurrent to the catalyst flow. The mesoporous oxide materials according to the present invention can additionally or alternately be useful in Fluid Catalytic Cracking (FCC) and/or Thermofor Catalytic Cracking (TCC) processes.

The TCC process is typically a moving bed process, and the TCC catalyst can generally be used as pellets or beads, typically having an average particle size (diameter) from about 1/64" to about 1/4". In typical TCC processes, active hot catalyst beads can progress downwardly (concurrently) with a hydrocarbon feedstock through a cracking reaction zone. The hydrocarbon products can be separated from the (coked) catalyst and recovered, with the (coked) catalyst typically being recovered at the lower end of the zone and being sent to a regeneration step. TCC conversion conditions may include one or more of an average reactor temperature (WABT/EIT) from about 450° C. to about 510° C.; a catalyst/oil volume ratio from about 2 to about 7; a (volumetric) reactor space velocity from about 1 $hr^{-1}$ to about 2.5 $hr^{-1}$; and a (volumetric) recycle to fresh feed ratio from 0 to about 0.5.

The FCC process is also typically a moving bed process, in which the cracking catalyst can generally be in the form of fine particles with an average particle size from about 10 microns to about 200 microns that can generally be suspended in the feed and propelled upward in a reaction zone. Thus a (typically relatively heavy) hydrocarbon feedstock (e.g., an atmospheric and/or vacuum gasoil) can be admixed with the cracking catalyst to provide a fluidized suspension and cracked in an elongated reactor, or riser, at elevated temperatures to convert at least a portion of the heavier hydrocarbon molecules in the feedstock into a mixture of lighter hydrocarbon products. The (typically gaseous) reaction products and used (spent) catalyst can be discharged from the riser into a separator (e.g., a cyclone unit), located within the upper section of an enclosed stripping vessel, or stripper, that is in fluid communication with the riser reactor, with the reaction products being conveyed to a product recovery zone and the spent catalyst entering a relatively dense catalyst bed within the lower section of the stripper. In order to remove entrained hydrocarbons from the used (spent) catalyst prior to regeneration, a (typically relatively inert) stripping gas (e.g., steam) can be passed through the catalyst bed in order to separate/desorb the entrained hydrocarbons, conveying them to the product recovery zone. The fluidizable catalyst in typical FCC processes can be continuously circulated between the riser and the regenerator and can serve to transfer heat from the latter to the former, thereby supplying at least a portion (as much as possible) of the thermal needs of the cracking reaction, which is an endothermic process.

FCC conversion conditions may include one or more of a riser top temperature from about 500° C. to about 595° C. (for example from about 520° C. to about 565° C. or from about 530° C. to about 550° C.); a catalyst/oil weight ratio from about 3 to about 12 (for example from about 4 to about 11 or from about 5 to about 10); and an average catalyst residence time in the riser from about 0.5 second to about 15 seconds (for example from about 1 second to about 10 seconds).

The hydrocarbon feedstock to be cracked may include, in whole or in part, a gasoil (e.g., light, medium, heavy, vacuum, and/or atmospheric) having an initial boiling point above about 400° F. (204° C.), a T50 boiling point (i.e., the point at which approximately 50 percent by weight boils, or becomes or is gaseous, under atmospheric pressure) of at least about 500° F. (260° C.), and an end boiling point of at least about 600° F. (316° C.). The feedstock can additionally or alternately include one or more of thermal oils, residual oils, cycle stocks, whole top crudes, partial crudes, tar sand oils, shale oils, synthetic fuels, heavy hydrocarbon fractions derived from the destructive hydrogenation of coal, tar, pitches, and/or asphalts, hydrotreated feedstocks derived therefrom, and the like. As should be appreciated by those skilled in the art, the distillation of higher boiling petroleum fractions above about 400° C. can generally be carried out under vacuum (i.e., at subatmospheric pressure), typically to avoid thermal cracking. The boiling temperatures utilized herein are thus conveniently expressed in terms of the boiling point corrected to atmospheric pressure. Further additionally or alternately, resid compositions and/or deeper cut gasoils, such as with relatively high metals contents, can be cracked using catalysts employing the aggregated zeolite materials of the invention.

Aggregates of zeolite Y, as described herein, may further additionally or alternately be used as (ad-/ab-)sorbent separators according to methods known in the art, for example, as described in U.S. Pat. No. 5,993,773. In certain sorbent separator applications, the zeolite Y aggregates may be molded, e.g., into spherical or columnar pellets, optionally in combination with a clay binder or the like, and then subjected to ion exchange with Group 1-2 ions (such as Li and/or Ca) and activated (for example, at about 400° C. for about 1 hour), e.g., to obtain a sorbent separator having a high adsorption performance, particularly regarding nitrogen adsorption. Still further additionally or alternately, aggregates of zeolite Y as described herein can be used in sorbent separator applications to separate and/or concentrate oxygen from a gas mixture of oxygen and nitrogen, e.g., by an adsorption method.

Additionally or alternately, the present invention can include one or more of the following embodiments.

Embodiment 1. A stabilized aggregated form of zeolite Y comprising small size primary crystallites of zeolite Y, wherein at least 80% of the primary crystallites are aggregated to form secondary particles, wherein the zeolite exhibits (i) a silica to alumina molar ratio of 4:1 or more (e.g., at least 5:1) and (ii) an alkali metal content of less than 4 wt % (e.g., less than about 3 wt %, less than about 2 wt %, less than about 1 wt %, or less than about 0.5 wt %) and/or a rare earth metal content of at least about 2 wt % (e.g., from about 2 wt % to about 20 wt %, at least about 4 wt %, or from about 4 wt % to about 10 wt %), wherein an average size of the secondary particles, as viewed from the external surface of the secondary particles, is about 0.8 micron or more (e.g., about 1.0 micron or more), and wherein at least one of the following conditions apply: (a) an average size of the primary crystallites in the secondary particles, as viewed from the external surface of the secondary particles, is about 0.5 micron or less (e.g., about 0.3 micron or less or about 0.2 micron or less); (b) at least 80% (e.g., at least 90%) of the secondary particles comprise at least 5 primary crystallites; and (c) in at least 80% of the secondary particles, a ratio of the average size of the secondary particles to the average size of the primary crystallites is at least 3:1 (e.g., at least 5:1 or at least 10:1).

Embodiment 2. A stabilized aggregated form of zeolite Y according to claim 1, wherein said secondary particles are essentially spherical in shape.

Embodiment 3. A stabilized aggregated form of zeolite Y according to any one of the previous embodiments, wherein at least 80% of said secondary particles have an aspect ratio between 0.7 and 1.

Embodiment 4. A stabilized aggregated form of zeolite Y according to any one of the previous embodiments, wherein the secondary particles have an external surface area of about 10 m$^2$/g or more (e.g., about 20 m$^2$/g or more).

Embodiment 5. A stabilized aggregated form of zeolite Y according to any one of the previous embodiments, wherein the secondary particles have central regions and edge regions, and wherein the central regions are less dense than the edge regions, as measured by SEM or TEM.

Embodiment 6. A stabilized aggregated form of zeolite Y according to any one of the previous embodiments, wherein Si/Al ratios throughout the secondary particles are approximately uniform, as measured by elemental mapping.

Embodiment 7. A stabilized aggregated form of zeolite Y according to any one of the previous embodiments, further comprising at least one hydrogenating metal component.

Embodiment 8. A stabilized aggregated form of zeolite Y according to any one of the previous embodiments, having a mesopore volume of at least about 0.03 cc/g.

Embodiment 9. A stabilized aggregated form of zeolite Y according to any one of the previous embodiments, wherein said zeolite Y has a unit cell size of about 25 Angstroms or less.

Embodiment 10. A stabilized aggregated form of zeolite Y according to any one of the previous embodiments, wherein said zeolite Y is prepared from a reaction mixture in which sodium silicate solution is used as a source of silica.

Embodiment 11. A stabilized aggregated form of zeolite Y according to any one of the previous embodiments, wherein said zeolite Y is prepared from a reaction mixture in which a precipitated silica powder is used as a source of silica.

Embodiment 12. A stabilized aggregated form of zeolite Y according to any one of the previous embodiments, wherein an aggregated form of the zeolite is stabilized by exchanging sodium ions with ammonium ions, followed by calcining the ammonium-exchanged aggregates at a temperature sufficient to decompose the ammonium.

Embodiment 13. A stabilized aggregated form of zeolite Y according to embodiment 12, wherein the calcined, ammonium-exchanged aggregates are steamed under sufficient steaming conditions to remove framework aluminum from the primary crystallites, wherein the steamed aggregates are optionally further acid treated by contact with an aqueous acid under conditions sufficient to remove non-framework aluminum from the aggregates, and wherein the acid treated aggregates, when formed, are optionally exposed to rare earth metal ions under conditions sufficient to incorporate at least 2 wt % of rare earth ions into and/or onto the aggregates.

Embodiment 14. A hydrocarbon conversion catalyst comprising a stabilized aggregate form of zeolite Y according to any one of the previous embodiments, in combination with a binder and/or matrix material.

Embodiment 15. A hydrocarbon conversion process comprising contacting a hydrocarbon-based feed with the hydrocarbon conversion catalyst of embodiment 14 or with a catalyst comprising a calcined version of a stabilized aggregate form of zeolite Y according to any one of embodiments 1-13.

EXAMPLES

Comparative Example 1A

Non-Aggregated NaY Recipe Under Static Conditions

A mixture was prepared from ~885 grams of water, ~262 grams of Ultrasil® silica, ~150 grams of sodium aluminate solution (45% in water), and ~167 grams of 50% sodium hydroxide solution (in water). The mixture had the following molar composition:

| | |
|---|---|
| $SiO_2/Al_2O_3$ | ~10.6 |
| $H_2O/SiO_2$ | ~15.1 |
| $OH^-/SiO_2$ | ~0.76 |
| $Na^+/SiO_2$ | ~0.76 |

Figure 1A:
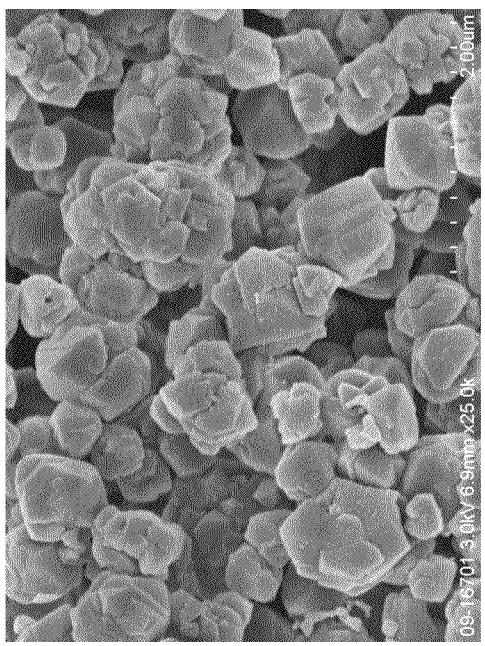

The mixture was first aged at room temperature (about 20-25° C.) for about 24 hours, while stirring at ~250 rpm. Then, the aged mixture was reacted at ~200° F. (~93° C.) in a ~2-liter autoclave without stirring for ~24 more hours. The product was filtered, washed with deionized (DI) water, and dried at ~250° F. (~120° C.). The X-ray diffraction pattern (XRD) pattern of the as-synthesized product material showed the typical phase of zeolite Y crystal topology. The SEM image of the as-synthesized product material showed that the material was composed of typical non-aggregated Y crystals, as shown in FIG. 1A. The as-synthesized Y crystals had a $SiO_2/Al_2O_3$ molar ratio of ~5.0 (measured at 4.96).

Comparative Example 1B

Non-Aggregated NaY Recipe with Stirring

A mixture was prepared from ~885 grams of water, ~262 grams of Ultrasil® silica, ~150 grams of sodium aluminate solution (45% in water), and ~167 grams of 50% sodium hydroxide solution (in water). The mixture had the following molar composition:

| | |
|---|---|
| $SiO_2/Al_2O_3$ | ~10.6 |
| $H_2O/SiO_2$ | ~15.1 |
| $OH^-/SiO_2$ | ~0.76 |
| $Na^+/SiO_2$ | ~0.76 |

The mixture was first aged at room temperature (about 20-25° C.) for about 24 hours, while stirring at ~250 rpm. Then, the aged mixture was reacted at ~200° F. (~93° C.) in a ~2-liter autoclave, while stirring at ~250 rpm, for ~24 more hours. The product was filtered, washed with deionized (DI) water, and dried at ~250° F. (~120° C.). The X-ray diffraction (XRD) pattern of the as-synthesized product material showed the typical phase of zeolite Y crystal topology with a trace of impurity phase of Gmelinite. The SEM image of the as-synthesized product material showed that the material was composed of typical non-aggregated Y crystals, of the type shown in FIG. 1B. The as-synthesized Y crystals had a $SiO_2/Al_2O_3$ molar ratio of ~5.12. No major differences in crystal size and morphology were observed compared with product of Comparative Example 1A based on the SEM data.

Example 2

Preparation of Aggregated NaY (Meso-Y) Crystals

A mixture was prepared from ~728 grams of water, ~275 grams of Ultrasil® silica, ~166 grams of sodium aluminate solution (45% in water), and ~120 grams of 50% sodium hydroxide solution (in water). The mixture had the following molar composition:

| | |
|---|---|
| $SiO_2/Al_2O_3$ | ~10.1 |
| $H_2O/SiO_2$ | ~12.1 |
| $OH^-/SiO_2$ | ~0.60 |
| $Na^+/SiO_2$ | ~0.60 |

Figure 2:
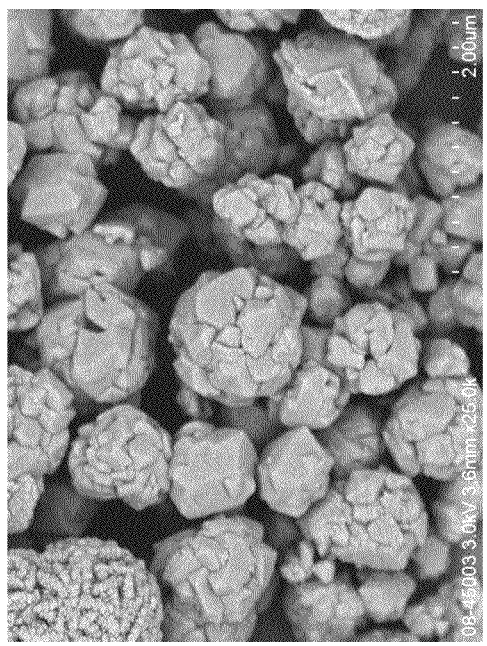
FIG. 2 shows a scanning electron microscope (SEM) image of a sample comprising a mixture of aggregated & non-aggregated NaY prepared according to Example 2.

The mixture was first aged at room temperature (about 20-25° C.) for about 24 hours, while stirring at ~250 rpm. Then, the aged mixture was reacted at ~176° F. (~80° C.) in a ~2-liter autoclave, while stirring at ~250 rpm, for ~192 more hours. The product was filtered, washed with deionized (DI) water, and dried at ~250° F. (~120° C.). The X-ray diffraction (XRD) pattern of the as-synthesized product material showed the typical phase of zeolite Y crystal topology with a very small trace of impurity phase of Gmelinite. The SEM image of the as-synthesized product material showed that the material was composed of aggregates of small crystals and non-aggregated crystals, as shown in FIG. 2. The as-synthesized Meso-Y crystals had a $SiO_2/Al_2O_3$ molar ratio of ~5.54 and a unit cell size (UCS) of approximately 24.61 Angstroms.

Example 3

Preparation of Non-Aggregated Na—Y Crystals from Diluted Reaction Mixture

A mixture was prepared from ~1000 grams of water, ~129 grams of Ultrasi® silica, ~49 grams of sodium aluminate solution (45% in water), and ~105 grams of 50% sodium hydroxide solution (in water). The mixture had the following molar composition:

| | |
|---|---|
| SiO$_2$/Al$_2$O$_3$ | ~16.2 |
| H$_2$O/SiO$_2$ | ~31 |
| OH$^-$/SiO$_2$ | ~0.82 |
| Na$^+$/SiO$_2$ | ~0.82 |

Figure 3:
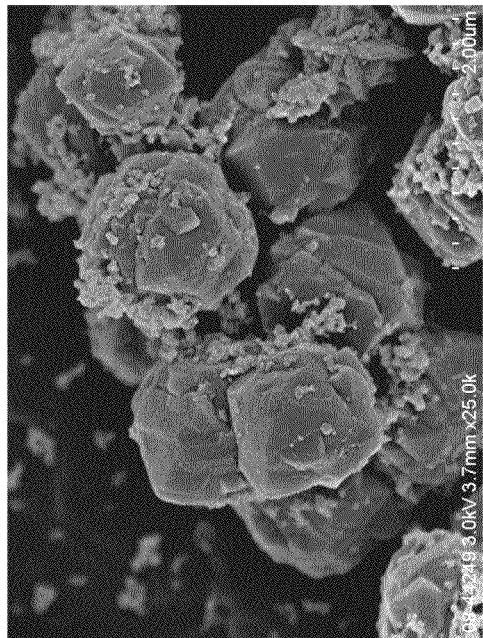
FIG. 3 shows a scanning electron microscope (SEM) image of a non-aggregated NaY sample prepared according to Example 3.

The mixture was first aged at room temperature (about 20-25° C.) for about 24 hours, while stirring at ~250 rpm. Then, the aged mixture was reacted at ~158° F. (~70° C.) in a ~2-liter autoclave, while stirring at ~250 rpm, for ~120 more hours. The product was filtered, washed with deionized (DI) water, and dried at ~250° F. (~120° C.). The X-ray diffraction (XRD) pattern of the as-synthesized product material showed the typical phase of zeolite Y crystal topology. The SEM image of the as-synthesized product material showed that the material was composed of typically Y non-aggregated crystal morphology, as shown in FIG. 3. The as-synthesized Meso-Y crystals had a SiO$_2$/Al$_2$O$_3$ molar ratio of ~4.64 and a unit cell size (UCS) of approximately 24.63 Angstroms.

Example 4

High-Solids Preparation of Aggregated Na—Y (Meso-Y) Crystals (Vs. Example 3)

A mixture was prepared from ~800 grams of water, ~258 grams of Ultrasil silica, 96 g of sodium aluminate solution (45%), and 210 g of 50% sodium hydroxide solution. The mixture had the following molar composition:

| | |
|---|---|
| SiO$_2$/Al$_2$O$_3$ | ~16.2 |
| H$_2$O/SiO$_2$ | ~14.1 |
| OH$^-$/SiO$_2$ | ~0.82 |
| Na$^+$/SiO$_2$ | ~0.82 |

Figure 4:
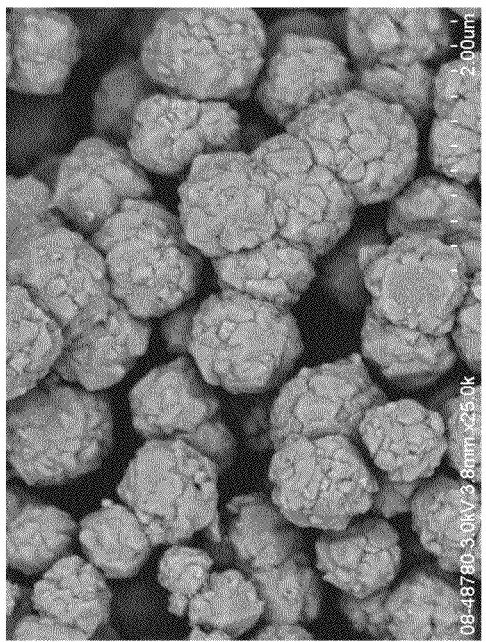
FIG. 4 shows a scanning electron microscope (SEM) image of a highly aggregated NaY sample prepared according to Example 4.

The mixture was first aged at room temperature (about 20-25° C.) for about 24 hours, while stirring at ~250 rpm. Then, the aged mixture was reacted at ~158° F. (~70° C.) in a ~2-liter autoclave, while stirring at ~250 rpm, for ~192 more hours. The product was filtered, washed with deionized (DI) water, and dried at ~250° F. (~120° C.). The X-ray diffraction (XRD) pattern of the as-synthesized product material showed the typical phase of zeolite Y crystal topology. The SEM image of the as-synthesized product material showed that the material was composed of aggregates of small crystals, as shown in FIG. 4. The as-synthesized Meso-Y crystals had a SiO$_2$/Al$_2$O$_3$ molar ratio of ~4.7 and a unit cell size (UCS) of approximately 24.68 Angstroms. A portion of the as-synthesized crystals were dried at ~250° F. (~120° C.) and then further calcined at ~540° C. for about 2-4 hours in air, without ion-exchanging. These calcined crystals showed total surface area of about 911 m$^2$/g, which included about 20 m$^2$/g of external surface area (compared to less than 10 m$^2$/g for conventional Na—Y preparations). In addition, another portion of the as-synthesized crystals were first ion-exchanged using-1N ammonium nitrate solution (in water) at room temperature to reduce sodium levels down to ~2%, and were then calcined at various temperatures (~600° C., ~700° C., —800° C., ~900° C., and ~1000° C.) in air for about 2-4 hours to stabilize their structures. Properties of those resulting products are shown in Table 1 below.

TABLE 1

Properties of partially-exchanged calcined Meso-Y from Example 4

| Calcination Temperature | Surface Area [m$^2$/g] (micro + external) | Alpha Value |
|---|---|---|
| ~600° C. | ~801/(~774 + ~27) | ~9.4 |
| ~700° C. | ~762/(~737 + ~25) | ~4 |
| ~800° C. | ~847/(~813 + ~34) | ~5.4 |
| ~900° C. | ~585(~535 + ~52) | ~0.85 |
| ~1000° C. | <~1 | N/A |

Alpha Value is an approximate indication of the catalytic cracking activity of the catalyst compared to a standard catalyst, and it gives the relative rate constant (rate of normal hexane conversion per volume of catalyst per unit time). It is based on the activity of silica-alumina cracking catalyst taken as an Alpha of 1 (Rate Constant≈0.016 sec$^{-1}$). The test for Alpha Value is described in U.S. Pat. No. 3,354,078 and in the *Journal of Catalysis* at 4, 527 (1965); 6, 278 (1966); and 61, 395 (1980), each incorporated herein by reference as to the relevant description. The experimental conditions of the Alpha Value test used herein include a constant temperature of about 538° C. and a variable flow rate as described in detail in the 1980 reference.

Example 5

Preparation of Aggregated NaY (Meso-Y) Crystals

A mixture was prepared from =830 grams of water, ~258 grams of Ultrasil® silica, ~96 grams of sodium aluminate solution (45% in water), and ~180 g of 50% sodium hydroxide solution (in water). The mixture had the following molar composition:

| | |
|---|---|
| SiO$_2$/Al$_2$O$_3$ | ~16.2 |
| H$_2$O/SiO$_2$ | ~14.2 |
| OH$^-$/SiO$_2$ | ~0.72 |
| Na$^+$/SiO$_2$ | ~0.72 |

Figure 5:
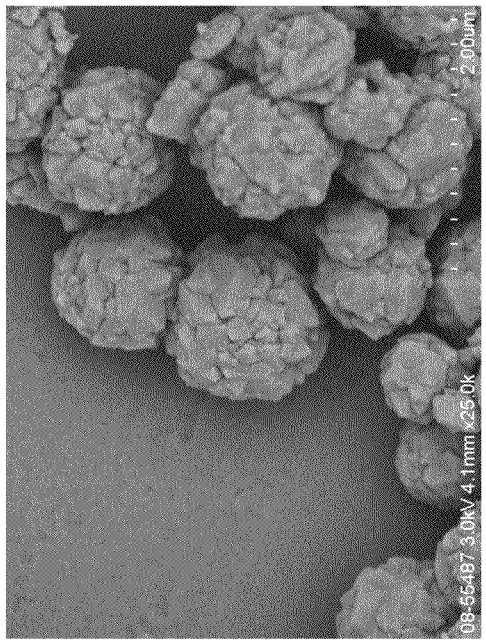
FIG. 5 shows a scanning electron microscope (SEM) image of a highly aggregated NaY sample prepared according to Example 5.

The mixture was first aged at room temperature (about 20-25° C.) for about 24 hours, while stirring at ~250 rpm. Then, the aged mixture was reacted at ~158° F. (~70° C.) in a ~2-liter autoclave, while stirring at ~250 rpm, for ~192 more hours. The product was filtered, washed with deionized (DI) water, and dried at ~250° F. (~120° C.). The X-ray diffraction (XRD) pattern of the as-synthesized product material showed the typical phase of zeolite Y crystal topology. The SEM image of the as-synthesized product material showed that the material was composed of aggregates (~1 micron) of small crystals, as shown in FIG. 5. The as-synthesized Meso-Y crystals had a SiO$_2$/Al$_2$O$_3$ molar ratio of ~5.6 and a unit cell size (UCS) of approximately 24.65 Angstroms. One portion of the as-synthesized crystals was ion-exchanged with ~1N ammonium nitrate solution (in water) at room temperature to reduce sodium levels down to ~2% and was then calcined various temperatures (~600° C. and ~800° C.) in air for about 24 hours to stabilize their structures. Other portions of the as-synthesized crystals were ion-exchanged with ~1N ammonium nitrate solution (in water) at room temperature to reduce sodium levels down to ~2% and were then steamed twice (i.e., 2x) at various temperatures (~600° C. and ~700° C.). To be clear, these other portions were ion-exchanged at room temperature, then steamed at a given temperature, then ion-exchanged at room temperature again, and then steamed at the given temperature again. Pore size distributions based on desorption isotherms from $N_2$ BET analysis of certain Table 2 samples are graphically depicted in FIG. 7 for comparison. Properties of those resulting products are shown in Table 2 below.

TABLE 2

Properties of stabilized zeolite Y from Example 5

| Series # (FIG. 7) | Calcination/Steaming Temperature | Surface Area [m²/g] (micro + external SA) | Alpha Value |
|---|---|---|---|
| 1 | Calc. ~600° C. w/o Steaming | ~840/(~814 + ~25) | ~26 |
| — | Calc. ~800° C. w/o Steaming | ~835/(~794 + ~41) | ~5.4 |
| 2 | Steam 2x ~600° C./ Ion-exchange | ~667/(~604 + ~64) | ~100 |
| 3 | Steam 2x ~700° C./ Ion-exchange | ~678/(~612 + ~67) | ~15 |

Figure 7:
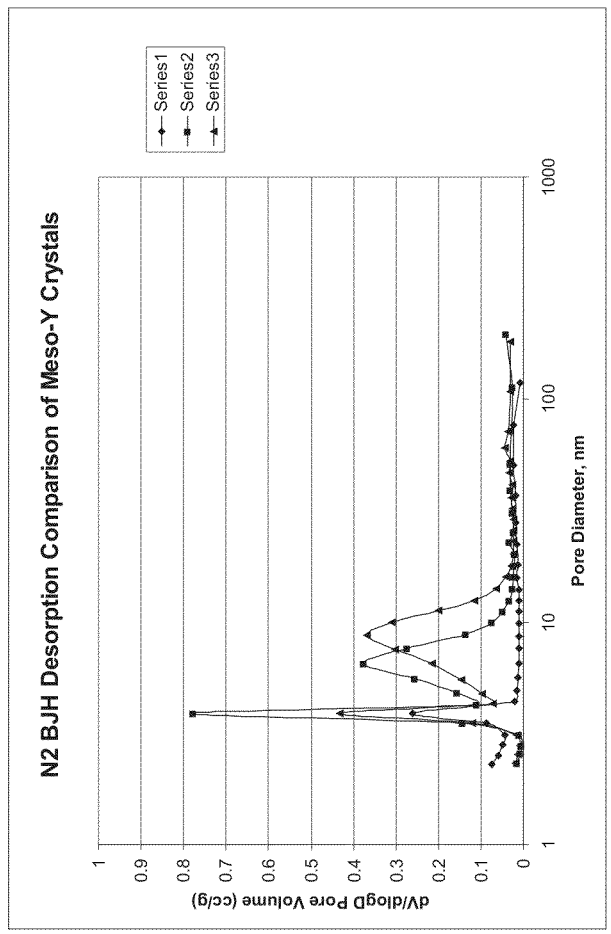
FIG. 7 shows a plot of pore size distributions based on BJH Desorption from $N_2$ BET analysis of samples: calcined at ~600° C., steamed treated at ~600° C., and steam treated at ~700° C., as prepared according to Example 6.

As clearly shown in FIG. 7, all three samples show a major peak at ~40 Angstroms, which (without being bound by theory) is believed to be associated with inter-crystal (or inter-primary particle) mesoporosity on steam-stabilized highly-aggregated Meso-Y products. For Series #1, this peak indicates the presence of high existing mesoporosity on calcined Meso-Y crystals even without a steam treatment. Typical stabilized zeolite Y (USY) products, however, tend to exhibit a very low ~40 Angstroms (inter-crystal) pore volume, which can classically be generated/increased either by relatively high temperature calcination or steaming treatments (intra-crystal mesoporosity may additionally be generated/increased by such treatments). In this Example, a relatively high intensity of existing mesoporosity on Meso-Y crystals prior to steam treatment was observed after calcination at ~600° C. or above. For steamed products, an increase of inter-crystal (alternately termed "primary particle") mesopore volume and a creation of an additional larger intra-crystal mean mesopore of at least 80 Angstroms were observed after both milder and high temperature steam treatments.

Example 6

Preparation of aggregated NaY (Meso-Y) crystals

A mixture was prepared from ~830 grams of water, ~258 grams of Ultrasil® silica, ~96 grams of sodium aluminate solution (45% in water), and ~180 grams of 50% sodium hydroxide solution (in water). The mixture had the following molar composition:

| | |
|---|---|
| $SiO_2/Al_2O_3$ | ~16.2 |
| $H_2O/SiO_2$ | ~14.2 |
| $OH^-/SiO_2$ | ~0.72 |
| $Na^+/SiO_2$ | ~0.72 |

Figure 6:
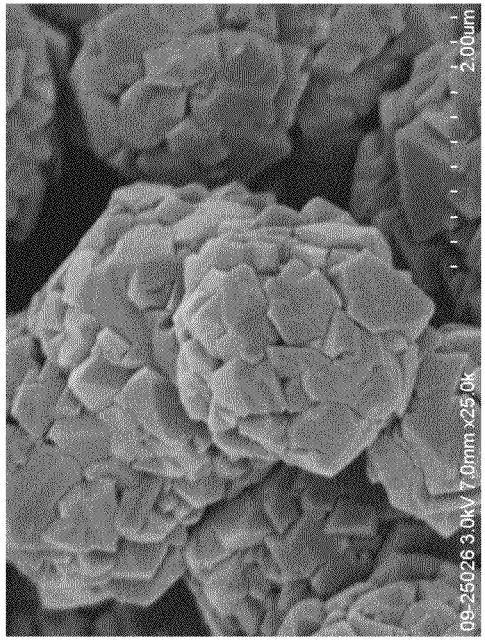
FIG. 6 shows a scanning electron microscope (SEM) image of a highly aggregated NaY sample prepared according to Example 6.

The mixture was first aged at room temperature (about 20-25° C.) for about 24 hours, while stirring at ~250 rpm. Then, the aged mixture was reacted at ~200° F. (~93° C.) in a ~2-liter autoclave under static conditions for ~120 more hours. The product was filtered, washed with deionized (DI) water, and dried at ~250° F. (~120° C.). The X-ray diffraction (XRD) pattern of the as-synthesized product material showed the typical phase of zeolite Y crystal topology. The SEM image of the as-synthesized product material showed that the material was composed of aggregates of small crystals with an aggregate (i.e., secondary) particle size of ~2 microns, as shown in FIG. 6, which is larger than the secondary particle size of the product of Example 5. The as-synthesized Y crystals had a $SiO_2/Al_2O_3$ molar ratio of ~5.5.

Example 7

Preparation of Aggregated NaY (Meso-Y) Crystals (~10× Scale-Up of Example 6)

A mixture was prepared from ~8.3 kilograms of water, ~2.58 kilograms of Ultrasil® silica, ~960 grams of sodium aluminate solution (45% in water), and ~1.8 kilograms of 50% sodium hydroxide solution (in water). The mixture had the following molar composition:

| | |
|---|---|
| $SiO_2/Al_2O_3$ | ~16.2 |
| $H_2O/SiO_2$ | ~14.2 |
| $OH^-/SiO_2$ | ~0.72 |
| $Na^+/SiO_2$ | ~0.72 |

Figure 8:
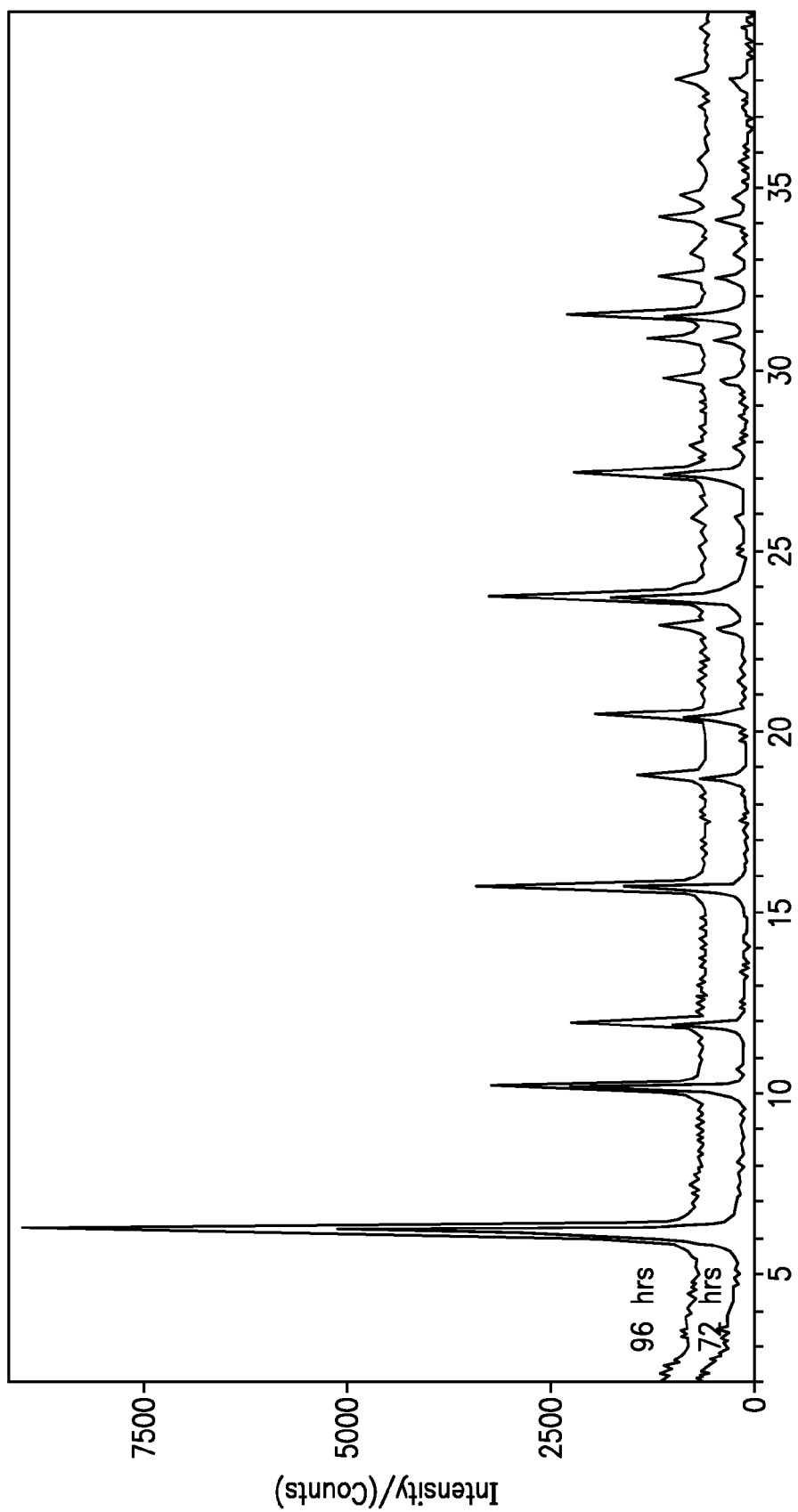
FIG. 8 shows XRD patterns of samples prepared according to Example 7.

The mixture was first aged at room temperature (about 20-25° C.) for about 24 hours, while stirring at ~250 rpm. Then, the aged mixture was reacted at ~200° F. (~93° C.) in a ~5-gallon autoclave under static conditions for ~96 more hours. The product was filtered, washed with deionized (DI) water, and dried at ~250° F. (~120° C.). The X-ray diffraction (XRD) patterns, as shown in FIG. 8, of as-synthesized product samples taken at ~72 hours and at ~96 hours showed the typical pure phase of zeolite Y crystal topology. Reaction appeared to be complete at less than ~96 hours. The resulting as-synthesized product crystals had a $SiO_2/Al_2O_3$ molar ratio of ~5.5.

Example 8

Stabilization by Mild Steaming Conditions on Meso-Y/Alumina Catalysts

About 65 parts of Meso-Y crystal prepared according to Example 7 having a silica/alumina molar ratio of ~5.5 were mixed with about 35 parts of Versal™ 300 pseudoboehmite alumina binder (basis: calcined at ~538° C.) in a Simpson™ muller. Sufficient water was added to produce an extrudable paste on a ~2" (~5.1 cm) diameter Bonnot™ extruder. The mixture of Meso-Y, pseudoboehmite alumina, and water was extruded into ~1/16" diameter quadrulobes, and then dried in a hotpack oven at ~121° C. overnight (for about 10-18 hours). The dried extrudate was calcined in nitrogen at ~538° C. and was then humidified with water-saturated air (~100% RH) and ion-exchanged with ~1N ammonium nitrate solution (in water) to remove sodium. After ammonium nitrate exchange, the extrudate was washed with deionized water to remove residual nitrate ions, prior to drying at ~121° C. overnight again and subsequent calcination in air at ~538° C. The resulting extrudates were then steamed at ~700° C. for about 4 hours, followed by additional ion-exchange to obtain the final extrudate for Pt impregnation. The final extrudate was then impregnated via incipient wetness to ~0.6 wt % Pt using tetraammineplatinumnitrate; followed by calcination in air for about 3 hours at ~680° F. (~405° C.).

Example 9

Decane Isomerization with Catalysts of Example 8

Figure 9:
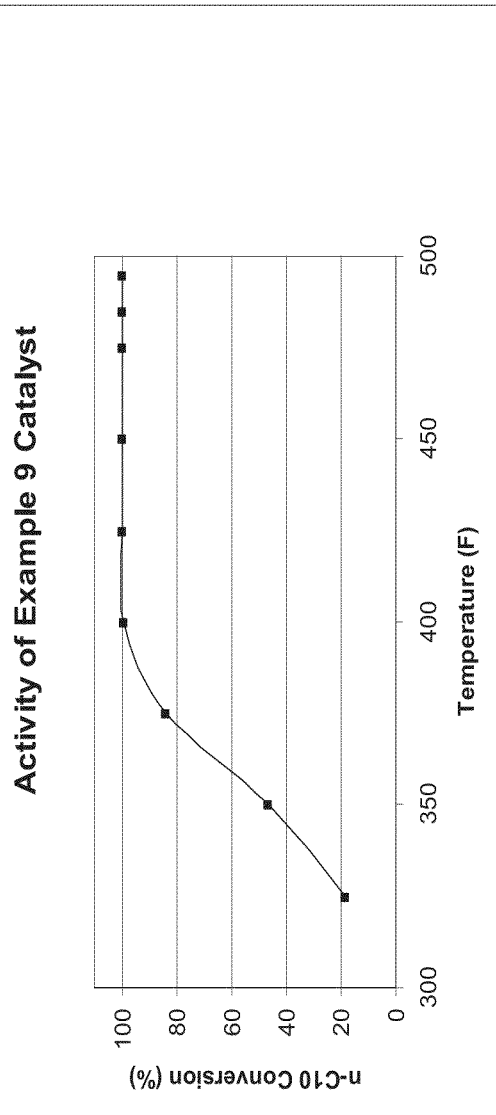
FIG. 9 depicts a plot showing n-decane isomerization activity for catalysts prepared according to Example 9.
Figure 10:
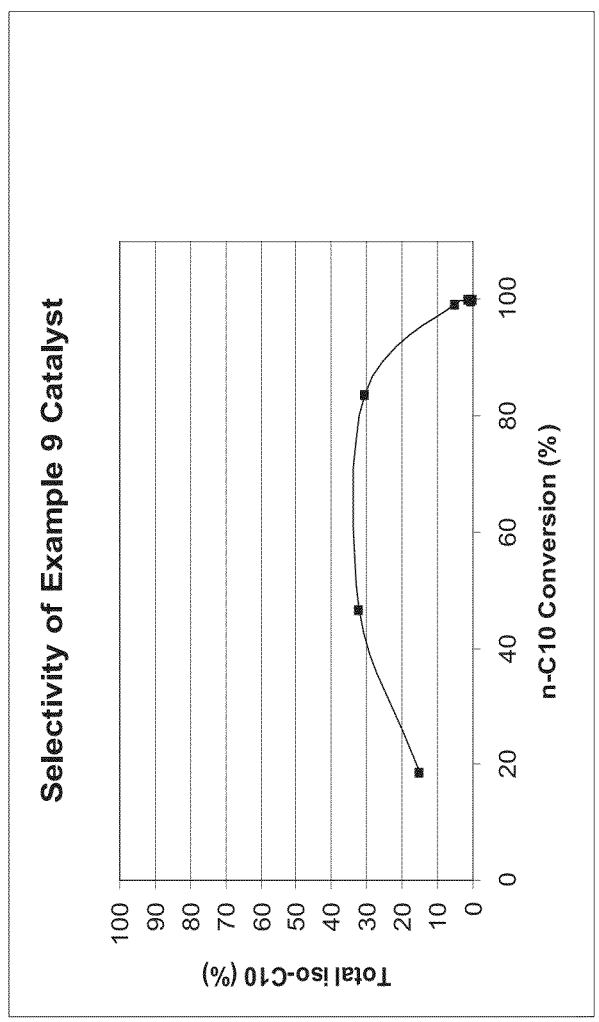
FIG. 10 depicts a plot showing n-decane isomerization selectivity for catalysts prepared according to Example 9.

Meso-Y catalyst of Example 8 was tested for dewaxing performance at atmospheric pressure in a quartz reactor vessel. Catalyst samples were crushed and sized to ~14/25 mesh, and ~1 gram of sized catalyst was used for this dewaxing test. Each sample was first heated under nitrogen to ~500° F. (~260° C.), followed by reduction in hydrogen for ~3 hours at atmospheric pressure (~0 psig). The temperature was then reduced to ~325° F. (~163° C.), and a feed flow of ~200 cm$^3$/min hydrogen gas and ~0.55 cm$^3$/hr liquid n-decane (delivered by a MFC and ISCO pump, respectively) was started. After lining the catalyst out at this temperature, the product from the reactor was analyzed by an on-line gas chromatograph (GC), and the reactor temperature was increased to the next setpoint. The catalyst was evaluated at a total of 9 different temperatures from ~325° F. (~163° C.) to ~495° F. (~257° C.). FIGS. 9 and 10 show the decane isomerization performance, specifically involving catalyst activity and selectivity, respectively.

Examples 10A-B

Stabilization of Meso-Y/Alumina Catalysts by >700° C. Steam Treatment

Figure 11:
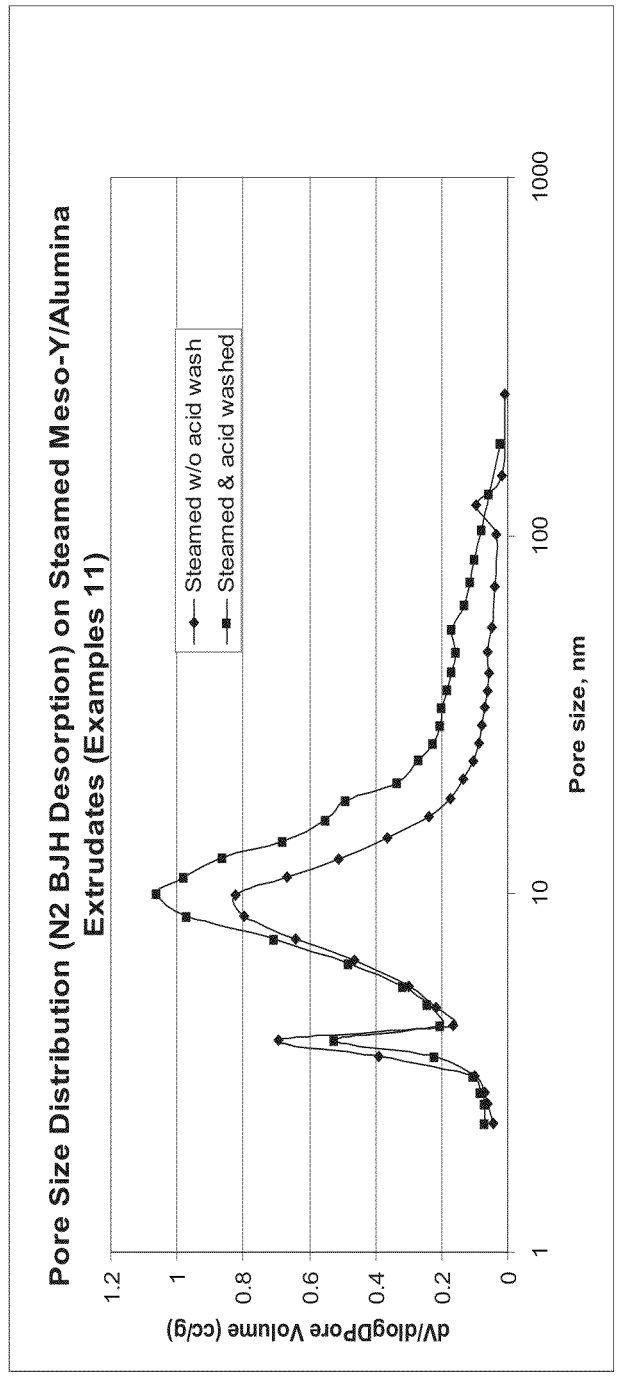
FIG. 11 depicts a plot of pore size distributions based on BJH Desorption from $N_2$ BET analysis of samples prepared according to Examples 10A-B.

About 65 parts of Meso-Y crystal prepared according to Example 7 having a silica/alumina molar ratio of ~5.5 were mixed with about 35 parts of Versal™ 300 pseudoboehmite alumina binder (basis: calcined at ~538° C.) in a Simpson™ muller. Sufficient water was added to produce an extrudable paste on a ~2" (~5.1 cm) diameter Bonnot™ extruder. The mixture of Meso-Y, pseudoboehmite alumina, and water was extruded into ~1/16" diameter quadrulobes, and then dried in a hotpack oven at ~121° C. overnight (for about 10-18 hours). The dried extrudate was calcined in nitrogen at ~538° C. and was then humidified with water-saturated air (~100% RH) and ion-exchanged with ~1N ammonium nitrate solution (in water) to lower sodium content. After ammonium nitrate exchange, the extrudate was washed with deionized water to remove residual nitrate ions, prior to drying at ~121° C. overnight again and subsequent calcination in air at ~538° C. The resulting extrudates were then steamed at ~760° C. for about 1 hour, followed by additional ion-exchange to obtain a treated extrudate. Properties of the treated extrudate included an Alpha Value of ~140, a UCS of ~24.52 Angstroms, and a total surface area of ~484 m$^2$/g (with a micropore surface area of ~307 m$^2$/g and an external surface area of ~177 m$^2$/g). The resulting treated extrudate was then steamed again at ~760° C. for about 16 hours, and a portion was washed with oxalic acid to remove non-framework alumina. The portion that was washed with oxalic acid is referred to herein as Meso-Y-B extrudate, and the other portion that was not washed is referred to herein as Meso-Y-A extrudate. The pore size distributions of these two extrudates are shown in FIG. 11. These extrudates were then each impregnated via incipient wetness to ~0.6 wt % Pt using tetraammineplatinumnitrate, followed by calcination in air for about 3 hours at ~680° F. (~405° C.).

Comparing FIGS. 7 and 11, more mesopore volume was found on steam treated extrudates bound with alumina. Also, more mesopore volume and broader pore size distribution appeared on the acid washed sample, which is consistent with BET surface area data (more external surface area). Also, higher Alpha value was found on the acid washed sample after removing non-framework Al atoms (or other species), as can be seen in Table 3 below.

TABLE 3

Properties of Meso-Y/alumina catalysts stabilized by steam treatment

| Catalyst | Surface Area [m$^2$/g] (micro + external SA) | Alpha Value | SiO$_2$/Al$_2$O$_3$/Na (wt ratio) |
|---|---|---|---|
| HT Stabilized Meso-Y-A[1] | 463/(295 + 167) | 2.4 | 40.7/34.8/0.52 |
| HT Stabilized Meso-Y-B[2] | 410/(201 + 209) | 9.4 | 52.5/42.4/0.17 |

[1]Steamed at ~760° C. for ~16 hours (without acid wash)
[2]Steamed at ~760° C. for ~16 hours (with oxalic acid wash)

Examples 11A-B

Decane Isomerization with Catalysts of Examples 10A-B

The Pt-impregnated Meso-Y-A and Meso-Y-B catalysts of Examples 10A-B were tested for dewaxing performance at atmospheric pressure in a quartz reactor vessel. Catalyst samples were crushed and sized to ~14/25 mesh, and ~1 gram of each sized catalyst was used for this dewaxing test. Each sample was first heated under nitrogen to ~500° F. (~260° C.), followed by reduction in hydrogen for ~3 hours at atmospheric pressure (~0 psig). The temperature was then reduced to ~325° F. (~163° C.), and a feed flow of ~200 cm$^3$/min hydrogen gas and ~0.55 cm$^3$/hr liquid n-decane (delivered by a MFC and ISCO pump, respectively) was started. After lining the catalyst out at this temperature, the product from the reactor was analyzed by an on-line gas chromatograph (GC), and the reactor temperature was increased to the next setpoint. Each catalyst was evaluated at a total of 9 different temperatures from ~325° F. (~163° C.) to ~495° F. (~257° C.).

Figure 13:
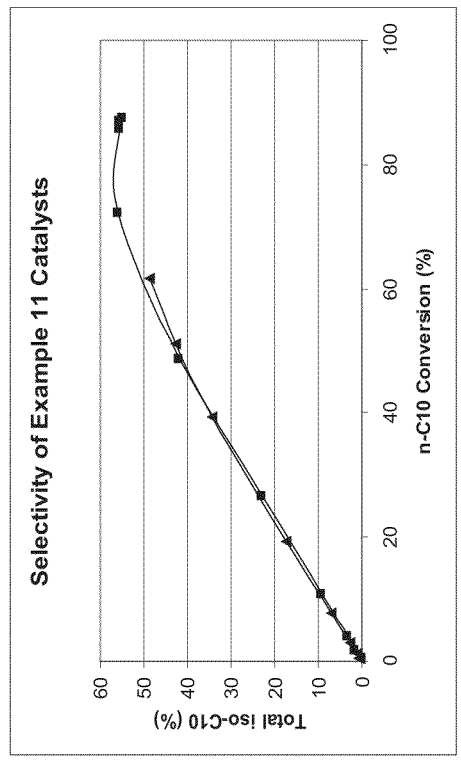
FIG. 13 depicts a plot showing n-decane isomerization selectivity for catalyst samples prepared according to Examples 10A-B.
Figure 12:
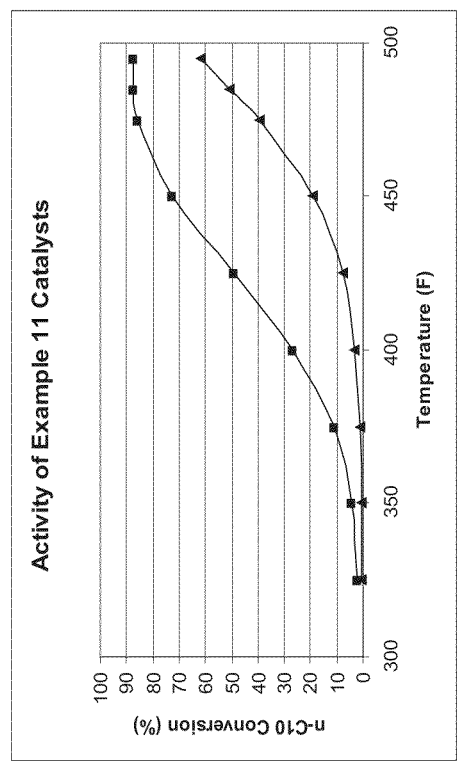
FIG. 12 depicts a plot showing n-decane isomerization activity for catalyst samples prepared according to Examples 10A-B.

FIGS. 12 and 13 show the decane isomerization performance, specifically involving catalyst activities and selectivities, respectively. From these Figures, it appears that the combination of steaming and acid wash treatments caused the tested catalyst samples to exhibit a dramatic increase in activity, even if only a marginal improvement in selectivity, over the merely steamed catalyst sample.

The foregoing Examples demonstrate that stabilized aggregates having relatively high surface areas with controlled inter- and/or intra-crystal mesoporosity were produced by relatively high temperature calcination and/or by steam post-treatment to attain lower sodium levels of the resulting crystals. The high temperature calcined product showed a significant increase in mesoporosity after the calcination at ~600° C. or above. For steamed products, an increase in inter-crystal mesopore volume and a growth in intracrystal mean mesopores (of >70 Angstroms) was observed after relatively high temperature steam treatment.

In addition, the n-decane isomerization results indicated that the steaming procedure used in the foregoing Examples (i.e., partial ion-exchange, followed by a ~1-hour steam treatment at ~760° C., followed by another ion-exchange, followed by a ~16-hour steam treatment at ~760° C., followed by an oxalic acid wash) offered performance advantages over conventional (e.g., lower temperature steaming steps at ~700° C. and/or no subsequent acid wash) steaming procedures. For instance, not only was isomerization activity improved but isomerization selectivity was also improved (e.g., from ~30-35% to ~55%, at ~70-80% conversion) using the aforementioned inventive steaming procedure.

Example 12

Stabilization by Partial Rare-Earth Ion-Exchange of Meso-Y (REMY)

REMY (partial rare-earth-exchanged Meso-Y) crystals were prepared by mixing ~200 grams of aggregated zeolite Y from Example 7 with ~3 kilograms of deionized (DI) water. About 40 grams of lanthanum trinitrate ($La(NO_3)_3$; ~8.6 wt % La to FAU) was added to the mixture, which was then heated to ~90° C. with stirring for ~2 hours. The resulting solid was filtered and washed with ample amounts of hot water. The resulting wet cake was calcined at ~500° C. in air for ~2 hours to give a partially rare-earth exchanged aggregated zeolite Y (REMY sample 1). About half of this calcined solid was then slurried with ~3 liters of ~1N aqueous $NH_4NO_3$ solution at ~50° C. and calcined again in air at ~300° C. to yield the $NH_4$-exchanged form (REMY sample 2).

Example 13

Stabilization by Complete Rare-Earth Ion-Exchange of Meso-Y (CREMY)

CREMY (complete rare-earth-exchanged Meso-Y) crystals were prepared by mixing about half of REMY sample 1 from Example 12 with ~1.5 kilograms of deionized (DI) water and about 20 grams of lanthanum trinitrate ($La(NO_3)_3$; ~8.6 wt % La to FAU). The mixture was then heated to ~90° C. with stirring for ~2 hours, from which a resulting solid was filtered and washed with ample amounts of hot water. The resulting wet cake was calcined at ~500° C. in air for ~2 hours to give a completely rare-earth exchanged aggregated zeolite Y (CREMY sample 1). A portion of this calcined solid was then slurried with ~3 liters of ~1N aqueous $NH_4NO_3$ solution at ~50° C. and calcined again in air at ~300° C. to yield the $NH_4$-exchanged form (CREMY sample 2). It should be understood that, though the CREMY samples in this Example are described as being "completely" ion-exchanged, the process may not result in all available exchange sites being substituted with a rare earth metal atom; in this case, "complete" is used more to indicate that the multi-step rare-earth exchange process has been completed on these samples, such that the resulting exchanged samples have attained the requisite level of desired stability. The properties of the aggregated Meso-Y (FAU framework type) samples and their ion-exchanged versions are shown in Table 4 below.

Temperature-Programmed Ammonia Adsorption (TPAA) is a measure of total acid site density of an acidic sample and was conducted herein using a Mettler TGA/SDTA 851 thermogravimetric analysis system at ambient pressure (~0 psig). Samples were first calcined in ~20 cm³/min flowing air to about 500° C. for about three hours, at least until a constant sample weight was obtained. The temperature of each sample was then reduced, while still maintaining air flow (though helium could alternately be used) to ~250° C. Next, each sample was allowed to equilibrate at the desired temperature (in this case, ~250° C.) in ~20 cm³/min flowing helium and weighed to provide a baseline for ammonia chemisorption. After being weighed, each sample was subjected to a number of pulses (~12 sec/pulse) of a gaseous mixture containing helium and (~10% v/v) ammonia until a constant weight was obtained. After each pulse of the gas mixture being tested, samples were flushed with the flowing helium for ~3 minutes. Approximately 20 separate pulses of the gas mixture were used in each test. The increase in weight of each sample in terms of milligrams of ammonia per gram of sample can be used to calculate the molar amount of $NH_3$ adsorbed per gram.

Example 14

Preparation of FCC Catalysts Using CREMY Crystals of Example 13

Fluid catalytic cracking catalysts were made by combining the CREMY zeolite crystals made according to Example 13 (about 35% by weight of the solid components) with a commercially available Gibbsite (matrix—about 20% by weight of the solid components), aluminum chlorohydrate (ACH binder—about 10% by weight of the solid components), Hydrite UF™ clay (inert filler—about 35% by weight of the solid components), and sufficient water to allow approximately spherical catalyst particles to be made from the resulting spray-dryable slurry formulation. The spray-dried catalyst particles were then ion-exchanged with ammonium sulfate, dried, and calcined at ~600° C. for ~1 hour to get the exchanged catalyst. The exchanged catalyst was then steam treated at ~760° C. for ~16 hours to form a CREMY FCC catalyst composition.

Example 15

FCC of Vacuum Gas Oil (VGO) Using CREMY Catalyst of Example 14

FCC of a VGO feedstock was conducted using a simulated fluidized bed reactor by contacting the (largely vaporized) VGO with ~1 gram of the CREMY formulated catalyst from Example 14 at a temperature of ~560° C., so as to attain a catalyst-feed contact time roughly on the order of a second. The feed injection rate was varied in order to screen the catalyst under different catalyst-to-oil ratios. After proper stripping, using nitrogen to separate heavy products from

TABLE 4

Properties of Meso-Y and its ion-exchanged versions

| Sample | Si/Al$_2$ (mol ratio) | Na [wt %] | La [wt %] | TPAA [mmol/g] | Total SA [m²/g] | Total PV [cm³/g] |
|---|---|---|---|---|---|---|
| as-synthesized Meso-Y | ~5.4 | ~7.05 | 0 | | ~895 | ~0.36 |
| REMY sample 1 | ~5.5 | ~3.75 | ~6.48 | ~0.40 | ~798 | ~0.33 |
| CREMY sample 1 | ~5.5 | ~1.66 | ~12.4 | ~0.52 | ~793 | ~0.33 |
| REMY sample 2 | ~5.8 | ~0.464 | ~6.39 | ~1.65 | ~857 | ~0.35 |
| CREMY sample 2 | ~5.9 | ~0.052 | ~11.4 | ~1.28 | ~800 | ~0.33 | spent catalyst, products were sent for analysis via a gas-liquid separation device. Coke was removed during an air burn out of the spent catalyst, and the amount (selectivity) of coke formed on the spent catalyst was calculated using IR data measuring the amount of $CO_2$ and CO generated.

Figure 14:
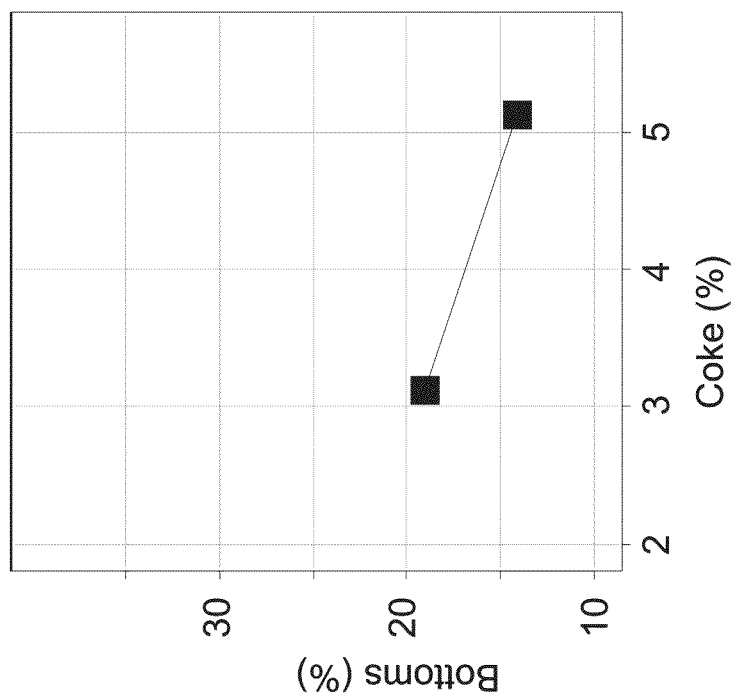
FIG. 14 depicts the bottoms selectivity vs. coke in FCC for a catalyst sample prepared according to Example 14.

The FCC performance data show that these aggregated faujasites were active in catalyzing bottoms conversion in FCC. See FIG. 14.

FIGS. 4-6 provide a perspective of secondary particles composed of primary crystallites in an aggregated form. The primary crystallites have an average size/width (i.e., a cross-sectional dimension in the plane of the SEM image) of ~0.3 micron or less. The depth (i.e., dimension perpendicular to the plane of the SEM image) of the primary crystallites was not readily quantifiable. The details of the interior regions of each secondary particle were also not readily observable from the SEM images. However, it can be observed that the average size of at least 80% (by number) of the secondary particles was about 0.8 micron or more. At least 5 primary crystallites were observable by SEM in at least 80% of the secondary particles. Also, the ratio of the average size of the secondary particles to the average size of the primary crystallites was at least 5:1 in at least 80% of the secondary particles.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A stabilized aggregated form of zeolite Y comprising small size primary crystallites of zeolite Y, wherein at least 80% of the primary crystallites are aggregated to form secondary particles, wherein the zeolite exhibits (i) a silica to alumina molar ratio of 4:1 or more and (ii) an alkali metal content of less than 4 wt % and/or a rare earth metal content of at least about 2 wt %, wherein an average size of the secondary particles, as viewed from the external surface of the secondary particles, is about 0.8 micron or more, and wherein at least one of the following conditions apply:
   (a) an average size of the primary crystallites in the secondary particles, as viewed from the external surface of the secondary particles, is about 0.5 micron or less;
   (b) at least 80% of the secondary particles comprise at least 5 primary crystallites; and
   (c) in at least 80% of the secondary particles, a ratio of the average size of the secondary particles to the average size of the primary crystallites is at least 3:1.

2. A stabilized aggregated form of zeolite Y according to claim 1, wherein the ratio of the average size of the secondary particles to the average size of the primary crystallites is at least 5:1, wherein the average size of the primary crystallites is about 0.3 micron or less, and wherein at least 90% of the primary crystallites are aggregated to form secondary particles.

3. A stabilized aggregated form of zeolite Y according to claim 1, wherein said secondary particles are essentially spherical in shape.

4. A stabilized aggregated form of zeolite Y according to claim 1, wherein at least 80% of said secondary particles have an aspect ratio between 0.7 and 1.

5. A stabilized aggregated form of zeolite Y according to claim 1, wherein the secondary particles have an external surface area of about 10 $m^2/g$ or more.

6. A stabilized aggregated form of zeolite Y according to claim 1, wherein the secondary particles have an external surface area of about 20 $m^2/g$ or more.

7. A stabilized aggregated form of zeolite Y according to claim 1, wherein the secondary particles have central regions and edge regions, and wherein the central regions are less dense than the edge regions, as measured by SEM or TEM.

8. A stabilized aggregated form of zeolite Y according to claim 1, wherein Si/Al ratios throughout the secondary particles are approximately uniform, as measured by elemental mapping.

9. A stabilized aggregated form of zeolite Y according to claim 1, wherein said zeolite Y exhibits a silica to alumina ratio of at least 5:1.

10. A stabilized aggregated form of zeolite Y according to claim 1, further comprising at least one hydrogenating metal component.

11. A stabilized aggregated form of zeolite Y according to claim 1, having a mesopore volume of at least about 0.03 cc/g.

12. A stabilized aggregated form of zeolite Y according to claim 1, wherein said zeolite Y has a unit cell size of about 25 Angstroms or less.

13. A stabilized aggregated form of zeolite Y according to claim 1, wherein said zeolite Y is prepared from a reaction mixture in which a sodium silicate solution is used as a source of silica.

14. A stabilized aggregated form of zeolite Y according to claim 1, wherein said zeolite Y is prepared from a reaction mixture in which a precipitated silica powder is used as a source of silica.

15. A stabilized aggregated form of zeolite Y according to claim 1, wherein an aggregated form of the zeolite is stabilized by exchanging sodium ions with ammonium ions, followed by calcining the ammonium-exchanged aggregates at a temperature sufficient to decompose the ammonium.

16. A stabilized aggregated form of zeolite Y according to claim 15, wherein the calcined, ammonium-exchanged aggregates are steamed under sufficient steaming conditions to remove framework aluminum from the primary crystallites.

17. A stabilized aggregated form of zeolite Y according to claim 16, wherein the steamed aggregates are further acid treated by contact with an aqueous acid under conditions sufficient to remove non-framework aluminum from the aggregates.

18. A stabilized aggregated form of zeolite Y according to claim 17, wherein the acid treated aggregates are exposed to rare earth metal ions under conditions sufficient to incorporate at least 2 wt % of rare earth ions into and/or onto the aggregates.

19. A hydrocarbon conversion catalyst comprising a stabilized aggregate form of zeolite Y according to claim 1, in combination with a binder and/or matrix material.

20. A hydrocarbon conversion catalyst comprising a stabilized aggregate form of zeolite Y according to claim 18, in combination with a binder and/or matrix material.

21. A hydrocarbon conversion process comprising contacting a hydrocarbon-based feed with a catalyst comprising a calcined version of a stabilized aggregate form of zeolite Y according to claim 1.

22. A hydrocarbon conversion process according to claim 21 wherein the catalyst is a dewaxing catalyst and the hydrocarbon conversion process comprises dewaxing a paraffinic feed with dewaxing reaction conditions including a temperature from about 200° C. (392° F.) to about 450° C. (842° F.), a pressure from about 0 psig to about 1000 psig (6.9 MPag), a WHSV from about 0.2 hr$^{-1}$ to about 10 hr$^{-1}$, and a hydrogen/hydrocarbon mole ratio from about 0.5 to about 10.

23. A hydrocarbon conversion process according to claim 21 wherein the catalyst is a isomerization catalyst and the hydrocarbon conversion process comprises isomerizing of olefins with isomerization reaction conditions including a temperature from about 250° C. (482° F.) to about 750° C. (1382° F.), an olefin partial pressure from about 30 kPa to about 300 kPa, and a WHSV from about 0.5 hr$^{-1}$ to about 500 hr$^{-1}$.

24. A hydrocarbon conversion process according to claim 22 wherein catalyst further comprises at least one Group 8-10 metal selected from Pt and Pd.

25. A hydrocarbon conversion process according to claim 23 wherein catalyst further comprises at least one Group 8-10 metal selected from Pt and Pd.

26. A hydrocarbon conversion process according to claim 22 wherein catalyst further comprises at least on Group 5-7 metal selected from Mo and W, and at least one Group 8-10 metal selected from Ni and Co.

27. A hydrocarbon conversion process according to claim 23 wherein catalyst further comprises at least one Group 5-7 metal selected from Mo and W, and at least one Group 8-10 metal selected from Ni and Co.

28. A hydrocarbon conversion process comprising contacting a hydrocarbon-based feed with a catalyst comprising a calcined version of a stabilized aggregate form of zeolite Y according to claim 18.

29. A hydrocarbon conversion process according to claim 28 wherein the catalyst is a fluid catalytic cracking (FCC) catalyst and the hydrocarbon conversion process comprises contacting the hydrocarbon-based feed with the catalyst in an FCC reactor riser including the process conditions of a riser top temperature from about 500° C. (932° F.) to about 595° C. (1103° F.), a catalyst/oil weight ratio from about 3 to about 12, and an average catalyst residence time in the riser from about 0.5 second to about 15 seconds.

30. A hydrocarbon conversion process according to claim 29 wherein the hydrocarbon-based feed is comprised of a heavy oil having an initial boiling point above about 400° F. (204° C.), a T50 boiling point of at least about 500° F. (260° C.), and an end boiling point of at least about 600° F. (316° C.).

31. A hydrocarbon conversion process according to claim 30 wherein the catalyst is a fluid catalytic cracking (FCC) catalyst includes a binder comprised of a clay.

32. A hydrocarbon conversion process according to claim 31 wherein the binder is further comprised of an inorganic oxide selected from silica, zirconia, titania, magnesia, beryllia, alumina, and mixtures thereof.

* * * * *